(12) United States Patent
Rubinstein et al.

(10) Patent No.: US 6,631,295 B2
(45) Date of Patent: Oct. 7, 2003

(54) SYSTEM AND METHOD FOR DIAGNOSING AND/OR REDUCING TINNITUS

(75) Inventors: Jay T. Rubinstein, Solon, IA (US); Carolyn J. Brown, Iowa City, IA (US); Richard S. Tyler, West Branch, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/961,690

(22) Filed: Sep. 25, 2001

(65) Prior Publication Data

US 2002/0091423 A1 Jul. 11, 2002

Related U.S. Application Data

(63) Continuation-in-part of application No. 09/373,785, filed on Aug. 13, 1999, now Pat. No. 6,295,472, which is a continuation-in-part of application No. 09/023,278, filed on Feb. 13, 1998, now Pat. No. 6,078,838.
(60) Provisional application No. 60/324,088, filed on Sep. 24, 2001.

(51) Int. Cl.[7] .............................................. A61N 1/36
(52) U.S. Cl. ............................................. 607/55
(58) Field of Search ........................ 607/55–57; 623/10; 600/25

(56) References Cited

U.S. PATENT DOCUMENTS

| | | | |
|---|---|---|---|
| 3,563,246 A | 2/1971 | Puharich et al. | 128/422 |
| 3,881,495 A | 5/1975 | Pannozzo et al. | 128/422 |
| 4,510,936 A | 4/1985 | Fourcin et al. | 128/419 |
| 4,515,158 A | 5/1985 | Patrick et al. | 128/419 |
| 4,577,641 A | 3/1986 | Hochmair et al. | 128/746 |
| 4,593,696 A | 6/1986 | Hochmair et al. | 128/419 |
| 4,611,596 A | 9/1986 | Wasserman | 128/419 |
| 4,648,403 A | 3/1987 | Van Compernolle | 128/419 |

(List continued on next page.)

FOREIGN PATENT DOCUMENTS

| | | |
|---|---|---|
| GB | 2 171 605 A | 9/1986 |
| WO | WO9600051 | 1/1996 |
| WO | WO9612383 | 4/1996 |

OTHER PUBLICATIONS

Ifukube et al., "Design Of An Implantable Tinnitus Suppressor By Electrical Cochlear Stimlation", Biomechanics, Rehabilation, Electrical Phenomena, Biomaterials, San Diego, Oct. 28–31, 1993, vol. 3, No. Conf. 15, pp. 1349–1350.

(List continued on next page.)

*Primary Examiner*—Jeffrey R. Jastrzab
(74) *Attorney, Agent, or Firm*—Fleshner & Kim, LLP

(57) ABSTRACT

A system and method for application of pseudospontaneous neural stimulation is provided that can generate stochastic independent activity across an excited nerve or neural population without an additional disadvantageous sensations. High rate pulse trains, for example, can produce random spike patterns in auditory nerve fibers that are statistically similar to those produced by spontaneous activity in the normal ear. This activity is called "pseudospontaneous activity". Varying rates of pseudospontaneous activity can be created by varying the intensity of a fixed amplitude, high rate pulse train stimulus, e.g., 5000 pps. A method and apparatus for diagnosing treatment for tinnitus with neural prosthetic devices according to the present invention that can use, for example, physiological responses to pseudospontaneous activity in an auditory nerve prior to the implementation of the neural prosthetic. Monitored patient response to the generated pseudospontaneous activity in the auditory nerve, even if temporary, can produce successful reduction or elimination in perceived tinnitus by subsequent treatment.

18 Claims, 15 Drawing Sheets

U.S. PATENT DOCUMENTS

| | | |
|---|---|---|
| 5,061,282 A | 10/1991 | Jacobs ........................... 623/10 |
| 5,095,904 A | 3/1992 | Seligman et al. ......... 128/420.6 |
| 5,215,085 A | 6/1993 | von Wallenberg-Pachaly .................... 128/420.6 |
| 5,271,397 A | 12/1993 | Seligman et al. ............ 607/137 |
| 5,549,658 A | 8/1996 | Shannon et al. ............... 607/57 |
| 5,571,148 A | 11/1996 | Loeb et al. .................... 607/40 |
| 5,597,380 A | 1/1997 | McDermott et al. ........... 607/57 |
| 5,601,617 A | 2/1997 | Loeb et al. .................... 607/56 |
| 5,649,970 A | 7/1997 | Loeb et al. .................... 607/57 |
| 5,697,975 A | 12/1997 | Howard, III et al. .......... 623/10 |
| 5,735,885 A | 4/1998 | Howard, III et al. .......... 607/55 |
| 6,078,838 A | 6/2000 | Rubinstein .................... 607/55 |

OTHER PUBLICATIONS

Cohen, N.L. et al., "A Prospective, Randomized Study of Cochlear Implants," *N. Engl. J. Med.*, 328:233–7,1993.

C.W. Parkins et al., "A Fiber Sum Modulation Code for a Cochlear Prosthesis" Annals of the New York Academy of Sciences, Jan. 1, 1983, vol. 405, pp. 490–501.

P.C. Loizou, "Signal Processing for Cochlear Prosthesis: A Tutorial Review", Proceedings of th $40^{th}$ Midwest Symposium on Circuits and Systems MWSCAS, IEEE 1997, pp. 881–885.

SYSTEM AND METHOD FOR DIAGNOSING AND/OR REDUCING TINNITUS

This application is a continuation-in-part application of U.S. Ser. No. 09/373,785 filed Aug. 13, 1999, U.S. Pat. No. 6,295,472 that issued on Sep. 25, 2001, which is a continuation-in-part application of U.S. Ser. No. 09/023,278 filed Feb. 13, 1998, U.S. Pat. No. 6,078,838 that issued on Jun. 20, 2000, and claims priority to U.S. Provisional Application 60/324,088, filed Sep. 24, 2001, the entire disclosure of each is incorporated herein by reference.

BACKGROUND OF THE INVENTION

1. Field of the Invention

This invention relates generally to an apparatus and method for providing stochastic independent neural stimulation, and in particular, a neural stimulation system and method for identifying candidates for intervention and treatment of tinnitus by initiating pseudospontaneous activity in the auditory nerve.

2. Background of the Related Art

Fundamental differences currently exist between electrical stimulation and acoustic stimulation of the auditory nerve. Electrical stimulation of the auditory nerve, for example, via a cochlear implant, generally results in more cross-fiber synchrony, less within fiber jitter, and less dynamic range, as compared with acoustic stimulation which occurs in individuals having normal hearing.

FIG. 1 shows the magnitude of a related art pattern of electrically-evoked compound action potentials (EAPs) from an auditory nerve of a human subject with an electrical stimulus of 1 kHz (1016 pulses/s). The EAP magnitudes are normalized to the magnitude of the first EAP in the record. FIG. 1 shows the typical alternating pattern previously described in the art. This pattern arises because of the refractory period of the nerve and can degrade the neural representation of the stimulus envelope. With a first stimulus 102 a large response occurs, likely because of synchronous activation of a large number of fibers. These fibers are subsequently refractory driving a second pulse 104, and accordingly a small response is generated. By the time of a third pulse 106, an increased pool of fibers becomes available (non-refractory) and the corresponding response increases. The alternating synchronized response pattern can be caused by a lack or decrease of spontaneous activity in the auditory nerve and can continue indefinitely.

Loss of spontaneous activity in the auditory nerve is one proposed mechanism for tinnitus. Proposed biological mechanisms for the loss of spontaneous activity in the auditory nerve include loss of hair cells in the cochlea. In addition, the loss of hair cells over time is a proposed mechanism for the loss of auditory neurons likely caused by related activities at synapses connecting the hair cells to the auditory neurons in the cochlea.

Tinnitus is a disorder where a patient experiences a sound sensation within the head ("a ringing in the ears") in the absence of an external stimulus. This uncontrollable ringing can be extremely uncomfortable and often results in severe disability. Restoration of spontaneous activity may potentially improve tinnitus suppression. Tinnitus is a very common disorder affecting an estimated 15% of the U.S. population according to the National Institutes for Health, 1989 National Strategic Research Plan. Hence, approximately 9 million Americans have clinically significant tinnitus with 2 million of those being severely disabled by the disorder.

Methods and apparatus that generate stochastically independent or "pseudospontaneous" neural activity in the auditory nerve have been modeled and tested with discernable improvements in auditory capabilities including reductions in tinnitus. See U.S. patent application Ser. No. 09/023,279 filed on Feb. 13, 1998, entitled "Speech Processing System and Method Using Pseudospontaneous Stimulation," which is hereby incorporated by reference. However, biological and somatosensory responses to gradual or rapid reversals of the loss of spontaneous activity in the auditory nerve, for example, were heretofore unknown. Preferably, pseudospontaneous neural activity would be introduced without perception to a patient. For example, in an auditory nerve the desired treatments of tinnitus associated with sensorineural hearing loss would suppress the tinnitus without producing any additional sensations and auditory percepts.

At this time the only clinically effective treatment that actually decreases the perception of tinnitus is acoustic masking. While this is helpful for some patients, for others it simply replaces one undesirable sound with another. An ideal therapy for tinnitus would create the perception of silence or at least decrease the loudness of tinnitus without introducing any new sounds. Further, there is no current method to identify successful treatment regimes based on tinnitus characteristics.

SUMMARY OF THE INVENTION

An object of the present invention is to provide an apparatus and method of neural stimulation that substantially reduces or obviates at least one of the problems caused by disadvantages of the related art.

Another object of the present invention is to provide an apparatus and method that imperceptibly generates stochastically independent or "pseudospontaneous" neural activity.

Yet another object of the present invention is to provide an apparatus and method that imperceptibly generates statistically independent or "pseudospontaneous" activity in an auditory nerve to suppress tinnitus.

Still yet another object of the present invention is to provide an inner ear or middle ear auditory prosthesis that suppresses tinnitus without producing additional sensations.

A further object of the present invention is to provide an apparatus and method that determines candidates for treatment of tinnitus using neural prosthetics.

A further object of the present invention is to provide an apparatus and method that determines candidates for treatment of tinnitus using neural prosthetics to generate pseudospontaneous activity in an auditory nerve.

A still further object of the present invention is to provide an apparatus and method that provides a diagnostic for significant reduction of tinnitus perceptions through treatment.

A still further object of the present invention is to provide an apparatus and method that tests whether a patient's tinnitus can be at least partially reduced.

A still further object of the present invention is to provide an apparatus and method that selects candidates for transtympanic electrical suppression of tinnitus.

A still further object of the present invention is to provide an apparatus and method that determines residual effects of applying signals capable of generating pseudospontaneous activity in a nerve.

To achieve at least the above objects in a whole or in parts, there is provided a method of diagnosing whether a human is a candidate for tinnitus reduction using a neural prosthetic, including applying an electrical signal capable of generating pseudospontaneous activity in an auditory nerve of at least one human to a plurality of candidates, identifying a prescribed threshold, and selecting the candidate having an auditory response to said electrical signal and tinnitus perception below the prescribed threshold upon application of said electrical signal.

To further achieve at least the above objects in a whole or in parts, there is provided a method of testing whether a patient's tinnitus can be at least partially reduced, including applying an electrical signal capable of generating pseudo-spontaneous activity in an auditory nerve of at least one human to the patient's auditory nerve, determining the patient's response to said electrical signal, and adjusting, if the patient's tinnitus is not at least partially reduced, a level of said electrical signal and repeating said determining step.

To further achieve at least the above objects in a whole or in parts, there is provided an apparatus of diagnosing whether a human is a candidate for tinnitus reduction using a neural prosthetic, including applying means for applying an electrical signal capable of generating pseudospontaneous activity in an auditory nerve of at least one human to a plurality of candidates, identifying means for identifying a prescribed threshold, and selecting means for selecting the candidate having an auditory response to said electrical signal and tinnitus perception below the prescribed threshold upon application of said electrical signal.

To further achieve at least the above objects in a whole or in parts, there is provided a method of determining residual effects to a patient with tinnitus resulting from application of a signal capable of inducing pseudo-spontaneous activity, including applying an electrical signal capable of generating pseudo-spontaneous activity in an auditory nerve of at least one human to the patient's auditory nerve for a first time period, and determining whether there remains a perceptible difference in the patient's tinnitus after said first time period.

To further achieve at least the above objects in a whole or in parts, there is provided a method for applying a high frequency signal to a nerve, including identifying a voltage level of high frequency signal that is sufficient to cause desired activity in the nerve, wherein the high frequency signal applied at said voltage level further is perceived as pain, modifying the high frequency signal to be the sufficient voltage level while the electrical signal remains substantially physiologically imperceptible to the patient, and applying the electrical signal to the auditory nerve to generate pseudospontaneous activity in the auditory nerve.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The auditory system is composed of many structural components, some of which are connected extensively by bundles of nerve fibers. The auditory system enables humans to extract usable information from sounds in the environment. By transducing acoustic signals into electrical signals, which are processed in the brain, humans can discriminate among a wide range of sounds with great precision.

Figure 1:
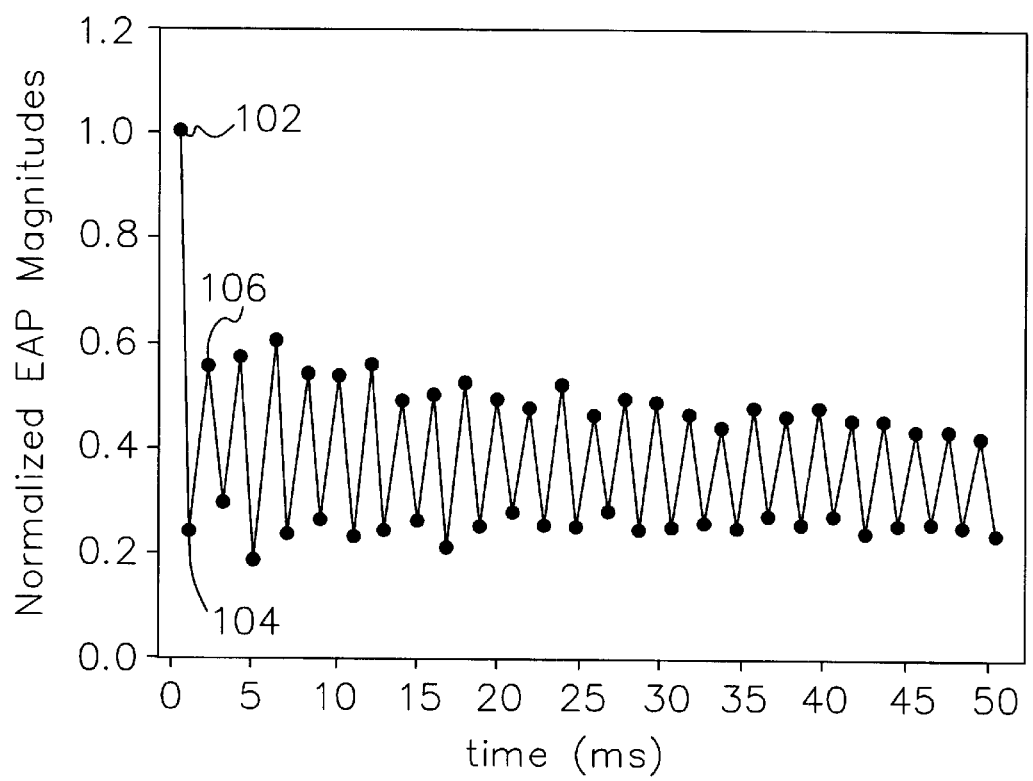
FIG. 1 is a diagram showing related art EAP N1P1 magnitudes in a human subject subjected to a low rate stimulus.
Figure 2:
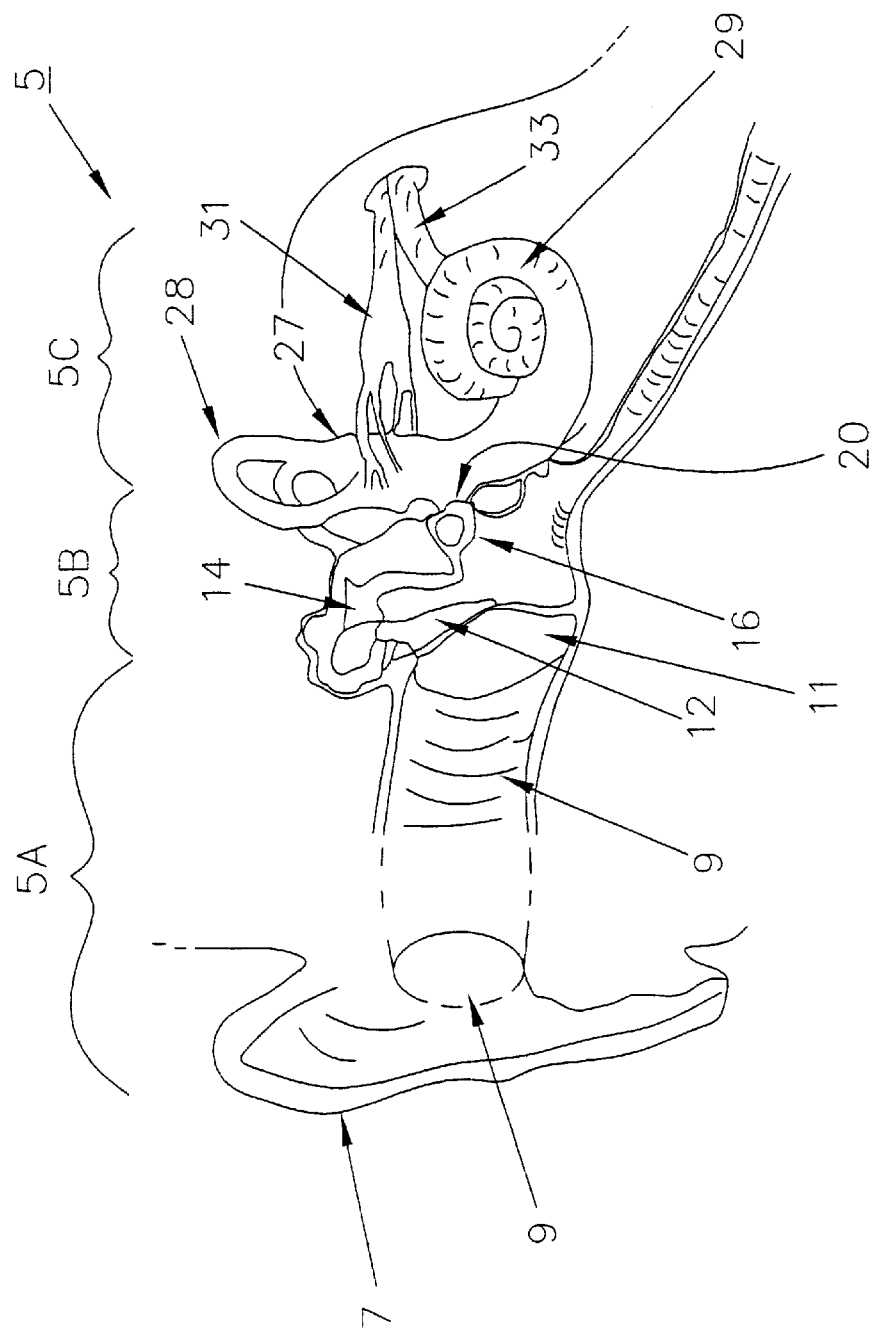
FIG. 2 is a diagram showing a section view of the human ear as seen from the front showing the relative positions of the hearing elements including the external ear, auditory cortex, cochlea and cochlear nucleus.

FIG. 2 shows a side cross-sectional view of a human ear 5, which includes the outer ear 5A, middle ear 5B and inner ear 5C. The outer ear 5A includes pinna 7 having folds of skin and cartilage and outer ear canal 9, which leads from the pinna 7 at its proximal end to the eardrum 11 at its distal end. The eardrum 11 includes a membrane extending across the distal end of the outer ear canal 9. The middle ear 5B is located between the eardrum 11 and the inner ear 5C and includes three small connected bones (ossicles), namely the hammer 12, the anvil 14, and the stirrup 16. The hammer 12 is connected to the inner portion of the eardrum 11, the stirrup 16 is attached to oval window 20, and the anvil 14 is located between and attached to each of the hammer 12 and the stirrup 16. A round or oval window 20 leads to the inner ear 5C. The inner ear 5C includes the labyrinth 27 and the cochlea 29, each of which is a fluid-filled chamber. The labyrinth 27, which is involved in balance, includes the semicircular canals 28. Vestibular nerve 31 attaches to the labyrinth 27. Cochlea 29 extends from the inner side of the round window 20 in a generally spiral configuration, and plays a key role in hearing by transducing vibrations transmitted from middle ear 5B into electrical signals for transmission along auditory nerve 33 to the hearing centers of the brain. The cochlea 29 is tonotopically organized, meaning different parts of the cochlea 29 respond optimally to different tones; one end of the cochlea 29 responds best to high frequency tones, while the other end responds best to low frequency tones. The cochlea 29 converts the tones to electrical signals that are then received by a cochlea nucleus (not shown), which is an auditory structure located in the brain.

In normal hearing, sound waves collected by the pinna 7 are funneled down the outer ear canal 9 and vibrate the eardrum 11. The vibration is passed to the ossicles (hammer 12, anvil 14, and stirrup 16). Vibrations pass through the round window 20 via the stirrup 16 causing the fluid within the cochlea 29 to vibrate. The cochlea 29 is equipped internally with a plurality of hair cells (not shown). Neurotransmitters released by the hair cells stimulate the auditory nerve 33 thereby initiating signal transmission along the auditory nerve 33. In normal hearing, the inner hair cell-spiral ganglion is inherently "noisy" in the absence of sound because of the random release of neurotransmitters from hair cells. Accordingly, in normal hearing, spontaneous activity in the auditory nerve occurs in the absence of sound.

Sound produces a slowly progressive response within and across fiber synchronization as sound intensity is increased. The absence of spontaneous activity in the auditory nerve can lead to tinnitus as well as other hearing-related problems.

Figure 3:
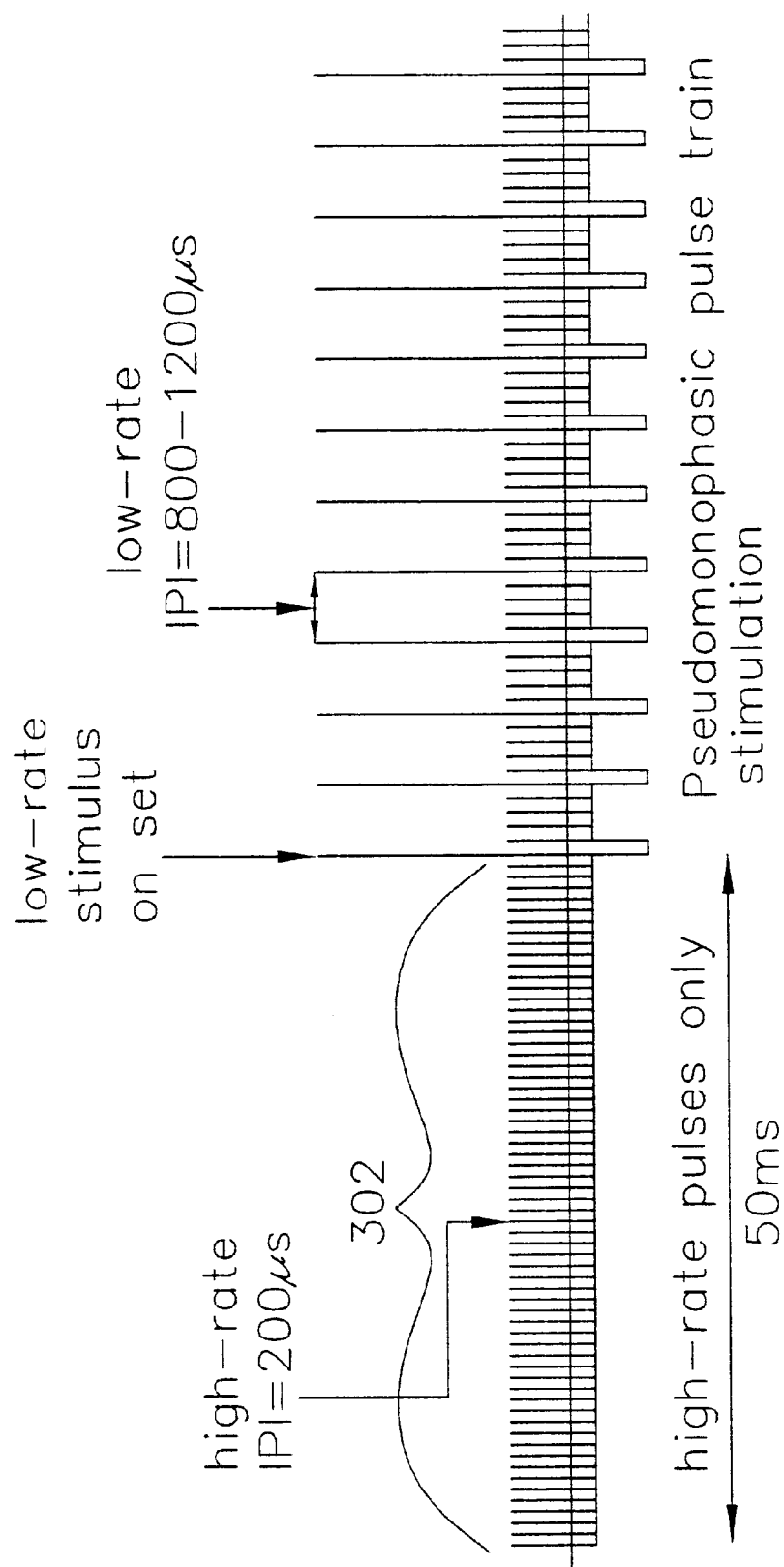
FIG. 3 is a diagram showing an exemplary embodiment of a driving signal that generates statistically independent activity in a nerve.

Preferred embodiments of the present invention emphasize delivery of stochastic independence across an excited neural population without introducing any additional audible or sensory percepts. An exemplary high rate pulse train driving signal 302 according to the first embodiment is shown in FIG. 3. However, broadband additive noise (e.g., because of rapid signal amplitude transitions), sinusoidal waves, and periodic signals can evoke pseudospontaneous activity similar to the high rate pulse train.

A population of 300 modelled auditory nerve fibers (ANF) has been simulated on a Cray C90 (vector processor) and IBM SP-2 (parallel processors) system. The ANF model used a stochastic representation of each node of Ranvier and a deterministic representation of the internode. Recordings were simulated at the 13th node of Ranvier, which approximately corresponds to the location of the porus of the internal auditory canal assuming the peripheral process has degenerated. Post-stimulus time (PST) histograms and interval histograms were constructed using 10 ms binning of the peak of the action potential. As is well-known in the art, a magnitude of the EAPs is measured by the absolute difference in a negative peak (N1) after pulse onsets and a positive peak (P2) after pulse onsets.

Stimuli presented to the ANF model were a high rate pulse train of 50 µs monophasic pulses presented at 5 kHz for 18 ms from a point source monopolar electrode located 500 µm perpendicularly from the peripheral terminals of the axon population. All acoustic nerve fibers were simulated as being in the same geometric location. Thus, each simulation can be considered to represent either 300 fibers undergoing one stimulus presentation or a single fiber undergoing 300 stimulus presentations. In addition, a first stimulus of the pulse train was of sufficient magnitude to evoke a highly synchronous spike in all 300 axons; all subsequent pulses are of an equal, smaller intensity. The first stimulus substantially increased computational efficiency by rendering all fibers refractory with the first pulse of the pulse train.

Two fibers were simulated for eight seconds using the parameters described above. Spike times were determined with one µs precision and assembled into 0.5 ms bins. Conditional mean histograms, hazard functions and forward recurrence time histograms were calculated (using 0.5 ms bins because of the small number of spikes (1000) simulated) as known to one of ordinary skill in the art. For example, see *Analysis of Discharges Recorded Simultaneously From Pairs of Auditory Nerve Fibers,* D. H. Johnson and N. Y. S. Kiang, Journal of Biophysics, 16, 1976, pages 719–734, (hereafter Johnson and Kiang), hereby incorporated by reference. See also *"Pseudospontaneous Activity: Stochastic Independence of Auditory Nerve Fibers with Electrical Stimulation,"* J. T. Rubinstein, et al., pages 1–18, 1998, hereby incorporated by reference.

Figure 4A:
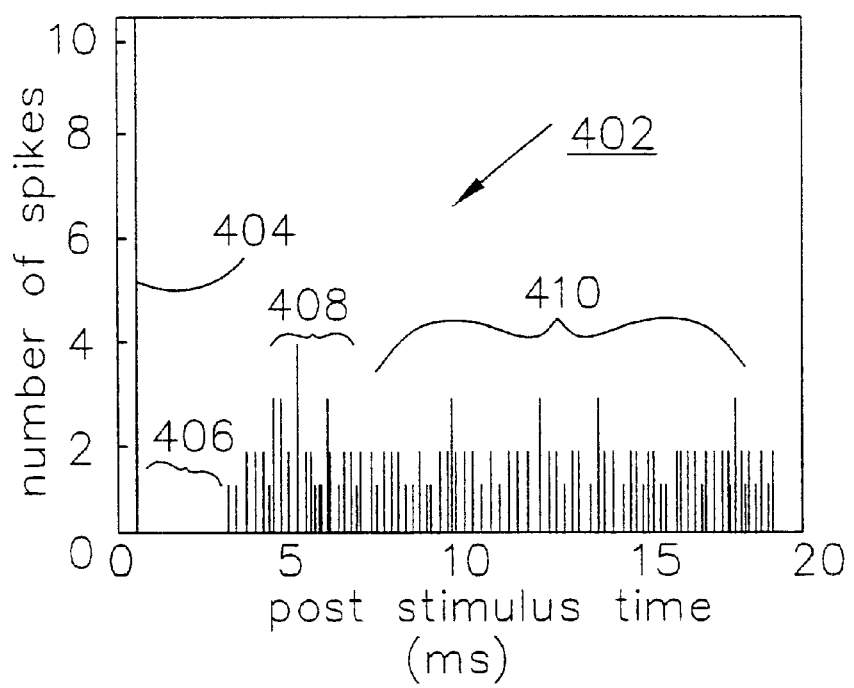
FIGS. 4A and 4B are diagrams showing histograms of modeled responses of the human auditory nerve to a high rate pulse train.

FIG. 4A shows a post-stimulus time (PST) histogram 402 of discharge times from the ANF model with a stimulus amplitude of 325 µA. A highly synchronous response 404 to a first, higher amplitude pulse was followed by a "dead time" 406. Then, an increased probability of firing 408 was followed by a fairly uniform firing probability 410. The y-axis of the PST histogram has been scaled to demonstrate temporal details following the highly synchronous response to the first pulse. There was a small degree of synchronization with the stimulus as measured by a vector strength of 0.26.

Figure 4B:
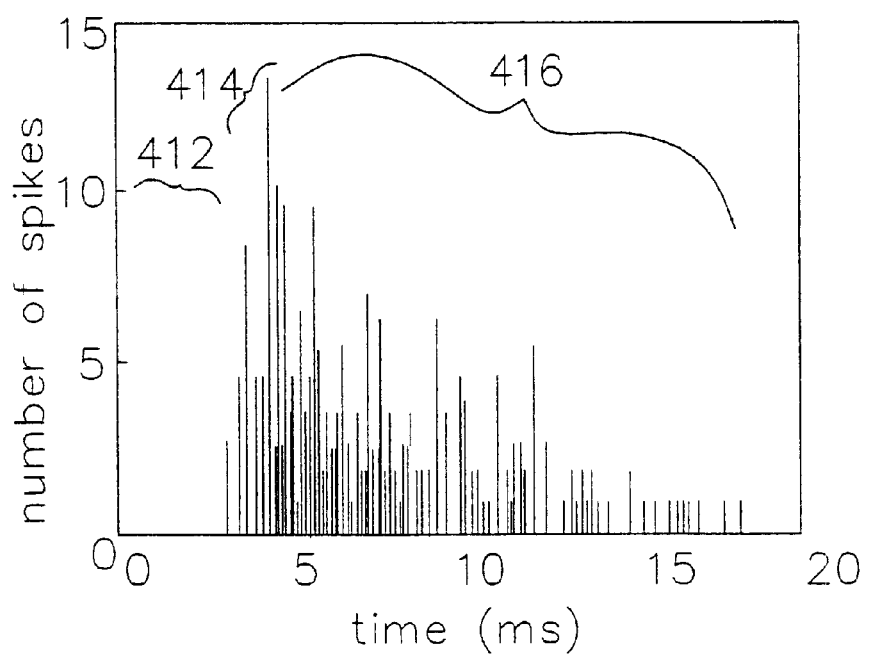

FIG. 4B shows an interval histogram of the same spike train. As shown in FIG. 4B, a dead time 412 was followed by a rapid increase in probability 414 and then an exponential decay 416. The interval histogram is consistent with a Poisson process following a dead time, a renewal process, and greatly resembles interval histograms of spontaneous activity in the intact auditory nerve. These simulation results correspond to a spontaneous rate of 116 spikes/second measured during the uniform response period of 7 to 17 ms.

Figure 5A:
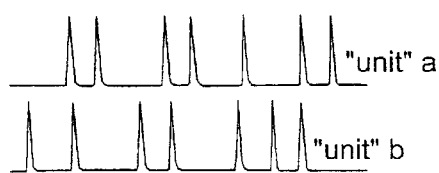
FIG. 5A is a diagram showing two exemplary unit waveforms.
Figure 5B:
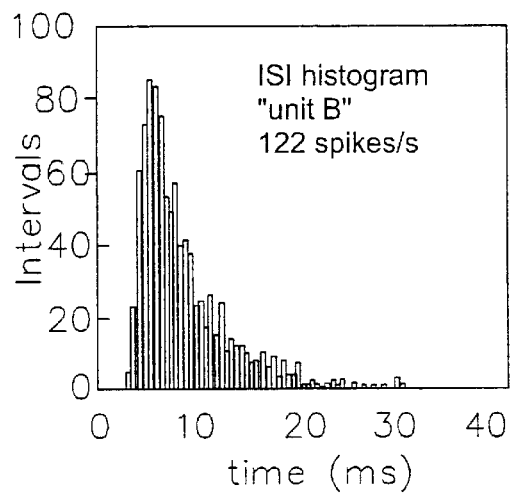
FIG. 5B is a diagram showing an interval histogram.
Figure 5C:
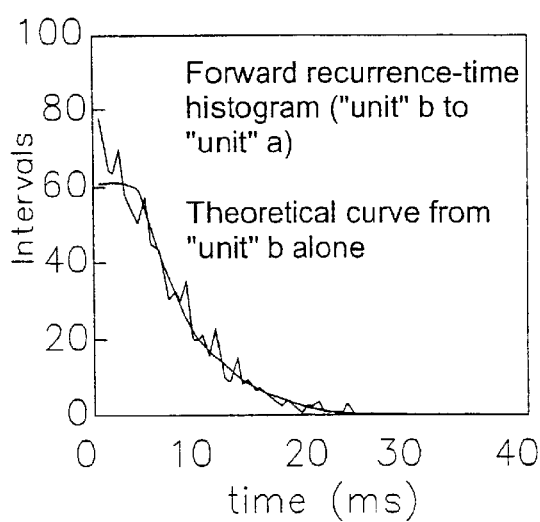
FIGS. 5C–5D are diagrams showing exemplary recurrence time data.
Figure 5D:
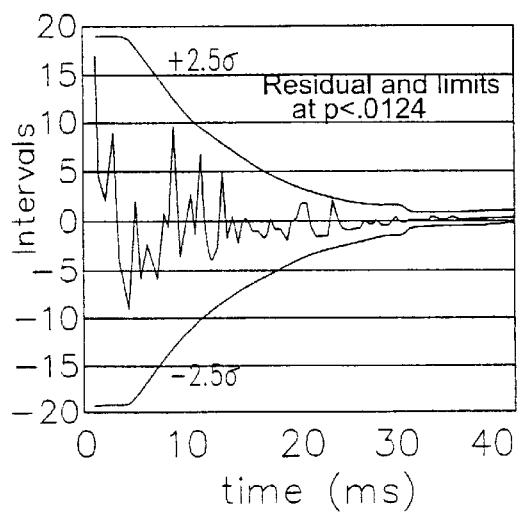

Normal spontaneous activity is independent across neurons. A rigorous evaluation of fiber independence is a recurrence-time test. (See, for example, Johnson and Kiang.) By using a bin size of 0.5 ms, useful recurrence-time histograms were assembled from two 2-second spike trains of the ANF model simulation. FIG. 5A shows a 50 ms sample of spike activity from two "units" (i.e., two simulated neurons). FIG. 5B shows an ISI histogram from an eight second run of "unit" b. FIG. 5C shows a forward recurrence-time histogram of "unit" b to "unit" a, and a theoretical recurrence-time from "unit" b assuming that "units" a and b are independent. The theoretical forward recurrence-time curve is flat during the refractory period. Theoretical limits are shown at $\rho<0.0124$ (2.5 standard deviations). FIG. 5D shows residuals calculated by subtracting the curves in FIG. 5C.

Driving a population of simulated auditory nerve fibers with high rate pulses according to an exemplary pseudospontaneous driving signal produces independent spike trains in each simulated fiber after about 20 ms. This pseudospontaneous activity is consistent with a renewal process and yields statistical data comparable to true spontaneous activity within computational limitations. Thus, the ANF model demonstrated pseudospontaneous activity caused by high rate pulse train stimulation. Further, any signal that results in pseudospontaneous activity that meets the same tests of independence as true spontaneous activity can be used as the driving signal.

According to the preferred embodiments of the present invention, the artificial induction of a random pattern of activation in the auditory nerve of a tinnitus patient or a hard-of-hearing patient mimics the spontaneous neural activation of the auditory nerve, which routinely occurs in an individual with normal hearing and lacking tinnitus. The artificially induced random pattern of activation of the auditory nerve is hereafter called "pseudospontaneous". In the case of an individual having a damaged cochlea, such induced pseudospontaneous stimulation activation of the auditory nerve may be achieved, for example, by the delivery of a high rate pulse train directly to the auditory nerve via a cochlea implant. Alternatively, in the case of a patient with a functional cochlea, pseudospontaneous stimulation of the auditory nerve may be induced directly by stimulation via an appropriate middle ear implantable device. Applicants have determined that high frequency signals of sufficient intensity to induce pseudospontaneous activity, desynchronizing the auditory nerve, and or alleviate the symptoms of tinnitus are substantially physiologically undetectable in a steady state condition of the patient. In dramatic and unanticipated contrast, the identical signals are physiologically and somatosensory detectable as uncomfortable pain, unpleasant noise and/or auditory percepts in a transient period. Such extreme opposite reactions do not appear to be explained using only a physical or only a psychological basis. However, preferred embodiments of a system and method for application of pseudospontaneous neural stimulation can control the transient period to provide a pseudospontaneous neural stimulation without producing an audible percept using inner ear and middle ear neural prosthetic devices, for example, to suppress tinnitus in the auditory nerve.

Preliminary studies by the Applicants showed remarkable but temporary auditory and sensory perceptual effects of a high frequency neural stimulation in human subjects. In one patient, a profoundly deaf individual with a cochlear implant, it was demonstrated that the loudness of a suprathreshold 5 kHz biphasic pulse train adapted substantially during continuous presentation. After about 2 or 3 minutes, depending on the stimulus conditions, the initially suprathreshold stimuli became inaudible. In a second patient with mild high frequency hearing loss and severe tinnitus, temporary placement of a promontory electrode stimulated by a 5 kHz biphasic pulse train repeatedly caused substantial but incomplete suppression of the subject's tinnitus with electrical stimulation. In the second patient, even after the stimulus was adapted to and became inaudible, the stimulus remained effective in reducing the tinnitus loudness.

Figure 6:
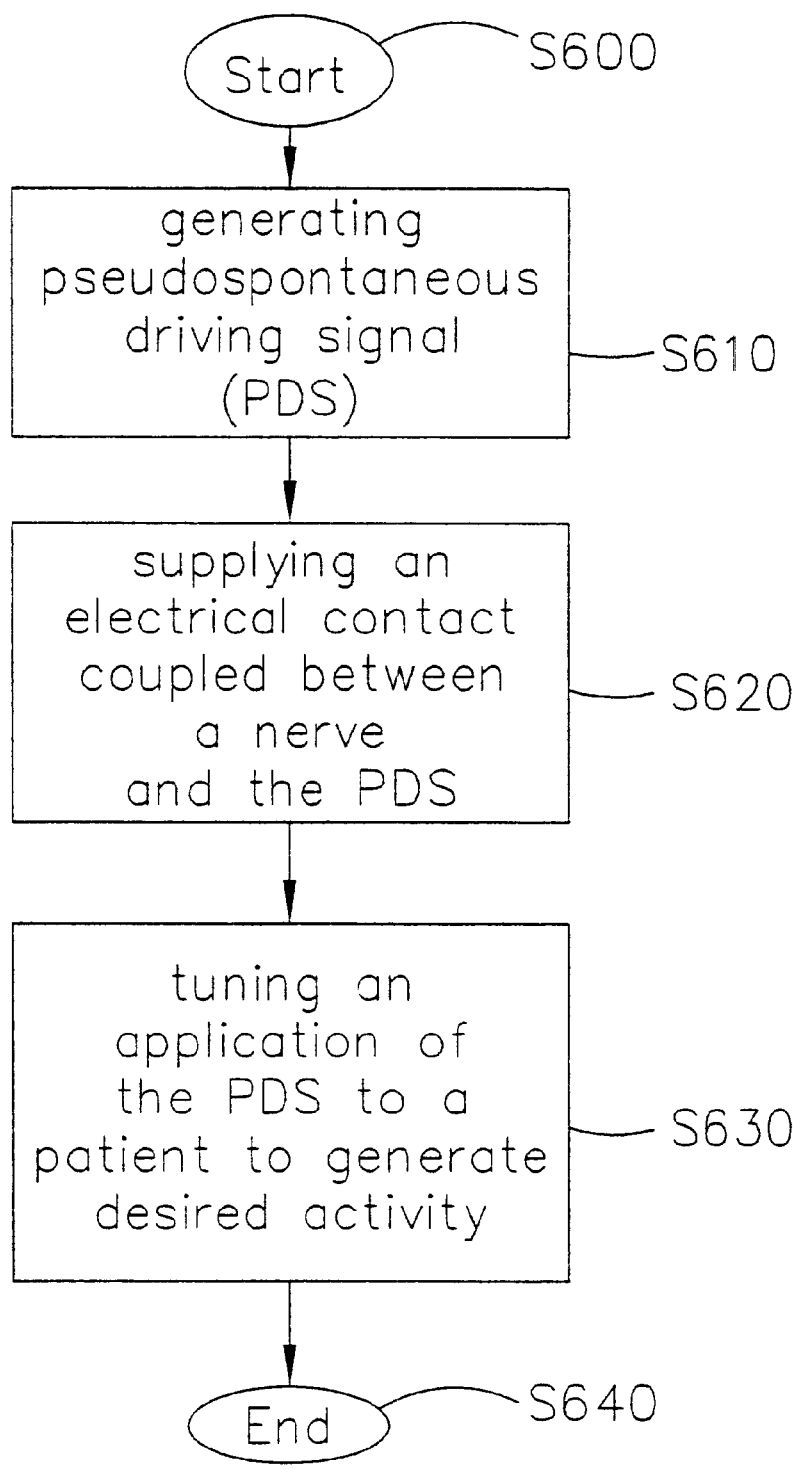
FIG. 6 is a diagram of a flowchart showing a preferred embodiment of a method of generating desired activity in a nerve of a patient.

A first preferred method for generating desired activity in a nerve according to the present invention will now be described. As shown in FIG. 6, the process starts in step S600. From step S600, control continues to step S610. In step S610, a pseudospontaneous driving signal (PDS) is generated. For example, a driving signal according to the first preferred embodiment can be generated or selected via a selection unit. An exemplary stimulus paradigm for a high-rate pulse train stimulation excepting the amplitude, frequency or interpulse period, which can be adjusted, is shown in FIG. 3. The high rate pulses 302 have a constant amplitude, pulse width and frequency of approximately 5 kHz as shown in FIG. 3. From step S610, control continues to step S620.

In step S620, an electrical contact is preferably coupled between a nerve such as the auditory nerve in the ear of a patient and the PDS. The electrical contact can be, for example, an electrode array having a plurality of contacts with a prescribed arrangement such as a tonotopic arrangement. Alternatively, a single electrode can be provided to the middle ear region and preferably at or near the round window as well as to the cochlea using a middle ear implant electrically coupled to the auditory nerve and cochlea in the inner ear or the like. From step S620, control continues to step S630.

In step S630, the application of the PDS is controlled or tuned to generate a desired activity in the nerve of a patient, for example, suppressing tinnitus in the auditory nerve. The control or tuning preferably accomplishes the application of the PDS to the nerve without generating additional sensations. For example, the tuning applies the PDS to the nerve without generating pain, or generating tolerable levels of pain (i.e., patient specific subjective amounts of pain) over a long term or a short term. From step S630, control continues to step S640 where the process is completed.

The controlled application of step S630, for example, can include a linear ramping from an initial imperceptible voltage level of the PDS at time zero to a desired voltage level that produces the intended activity in the nerve at time sufficiently after the time zero. The controlled application step according to the first preferred embodiment can optionally include a feed-back test loop to modify or merely select one of a plurality of selectable pseudospontaneous driving signals based on a subset of parameters specifically designed, determined and tested for an individual patient. For example, an exemplary controlled application in step S630 of a PDS according to the first preferred embodiment can suppress or reduce tinnitus without producing any additional sensation such as pain or audible noises to the patient.

The PDS signal at a prescribed level has also generated pain when applied to a sensory nerve. In particular, an exemplary PDS signal applied at 1–2 milliamps to the tongue generated mild pain for approximately 2 seconds. However, when the PDS signal was ramped manually to 1–2 milliamps over a range of seconds such as 5 seconds, application of the 1–2 milliamp PDS signal was not detected (i.e., pain free). However, the rate of firing of the nerves of the tongue may preclude pseudospontaneous activity.

Figure 7:
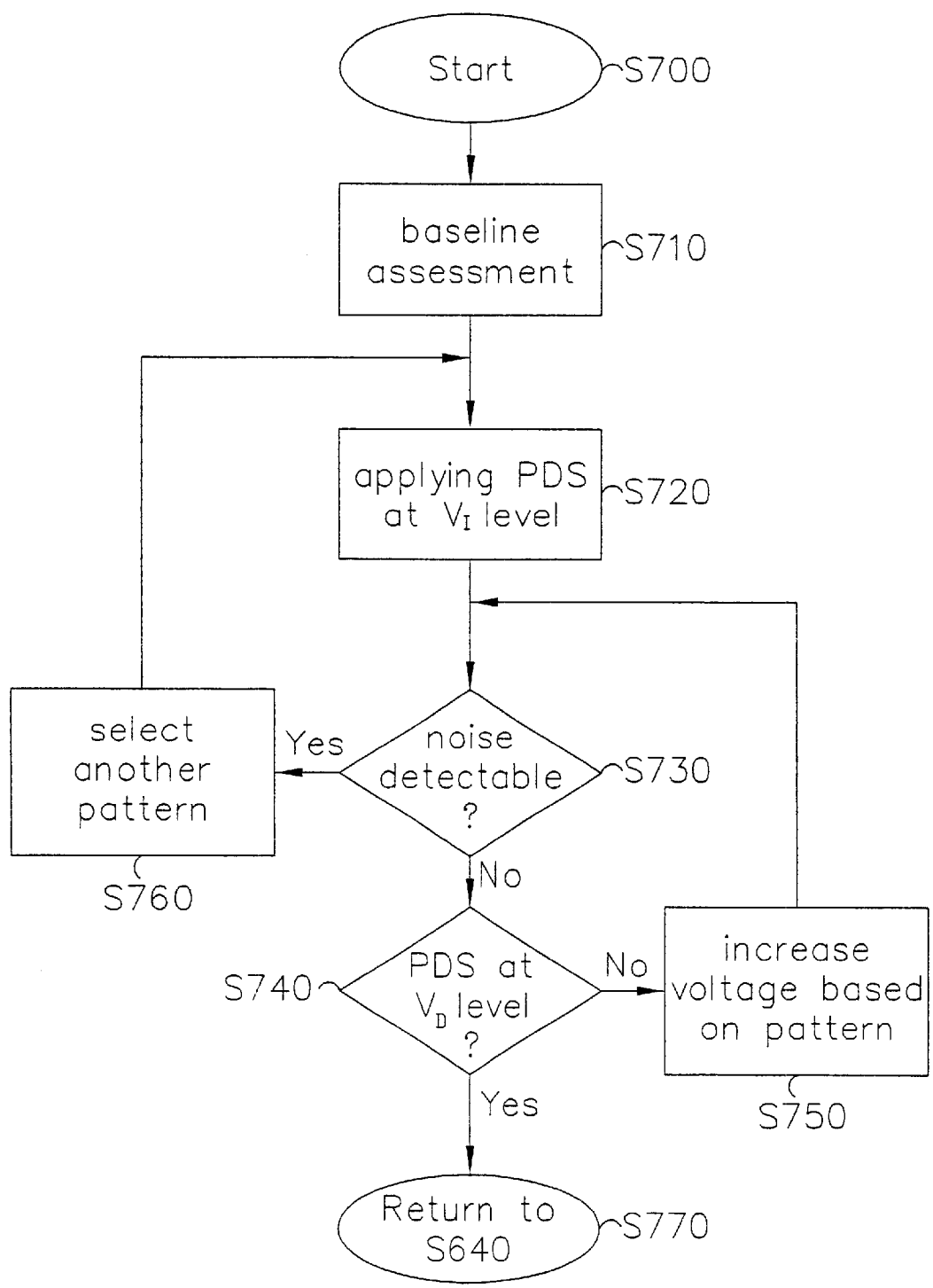
FIG. 7 is a diagram of a flowchart showing a preferred embodiment of a controlled application process to suppress tinnitus in an auditory nerve.

FIG. 7 shows a first preferred embodiment of the controlled application process of step S630 to suppress tinnitus in an auditory nerve. In step S700, the process begins. From step S700, control continues to step S710 where an appropriate baseline measurement of the auditory nerve of the patient is performed. Since the desired activity according to the first preferred embodiment of the controlled application step shown in FIG. 7 is to suppress tinnitus in the auditory nerve, two exemplary types of tinnitus patients will be described. One tinnitus patient type has severe-profound hearing loss treated by cochlear implantation and electrical stimulation will be via a cochlear implant. The second tinnitus patient type has mild-moderate high-frequency sensorineural hearing loss and electrical stimulation will be via an acutely placed transtympanic round window electrode or promontory electrode. Accordingly, in step S710, assessment procedures including at least one of a level of hearing ability and a level of tinnitus will be determined for each patient regardless of type of tinnitus. However, the two types preferably undergo different baseline or pre-stimulation assessments.

Preferably, all mild-moderate subjects are baselined by a medical evaluation, standard audiometry, and measures of spontaneous and click-evoked otoacoustic emissions. All subjects regardless of tinnitus type should complete the Tinnitus Handicap Questionnaire or the like. The Tinnitus Handicap Questionnaire is reliable and its psychometric properties have been previously evaluated using tinnitus sufferers as is known to one of ordinary skill in the art. These measures will allow comparison of tinnitus severity across all subjects independent of subsequent loudness measures. All subjects preferably complete a loudness scaling assessment by reporting the loudness of their tinnitus using a previously evaluated scaling technique on a 100 point scale: 0 corresponding to "no tinnitus" and 100 corresponding to the "loudest tinnitus imaginable". During subsequent electrical stimulation, loudness scaling for tinnitus as well as any electrically-induced percepts will be repeated in all subjects at all current or stimulation levels.

In addition to the questionnaire and the loudness scaling measures, the round window stimulation (mild-moderate) subjects preferably undergo extensive pre-stimulation psychophysical testing as part of baseline assessment. Loudness and dominant pitch of tinnitus will be assessed by comparison with tones presented to the contralateral ear. The amount of broadband noise required to mask the tinnitus in each ear could also be determined. In unilateral tinnitus, similar broadband noise levels required for masking across ears is suggestive of a central etiology. In bilateral tinnitus, the ability of a unilateral masker to suppress tinnitus bilaterally also suggests a central process. Psychophysical tuning curves for masking with tones and narrow-band noise can be performed both for the tinnitus and for tones of matching loudness and pitch. A "critical bandwidth" measurement for noise masking will preferably also be attempted. These latter two measures can be used to determine if the subject's tinnitus behaves consistently with a peripheral source. Correlations of such localization tests with an electrical suppression can also be evaluated based on assessment and treatment of a sufficient sample. Upon completion of a baseline assessment process in step S710, control continues to step S720.

Figure 8:
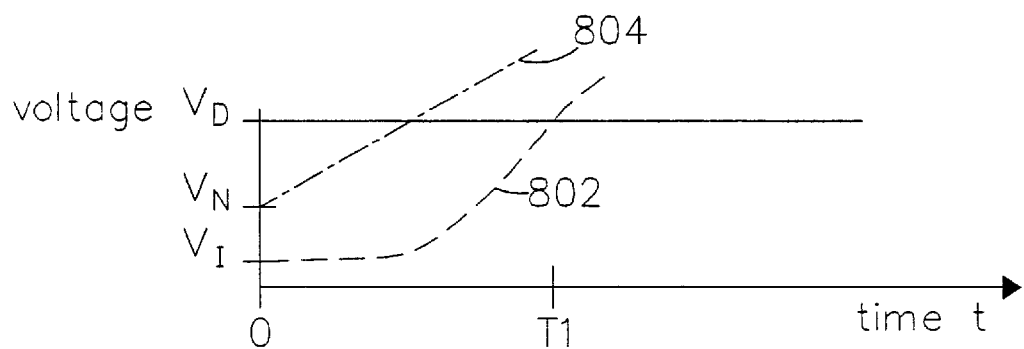
FIG. 8 is a diagram showing an exemplary driving signal voltage application pattern.

In step S720, application of the PDS signal at an initial voltage $V_I$ is provided to the auditory nerve of the patient. For example, as shown in FIG. 8, the initial voltage $V_I$ can be a level sufficiently small to insure pseudospontaneous activity is not generated in the auditory nerve. Alternatively, the initial voltage $V_I$ could be such that extremely localized pseudospontaneous activity is generated in the nerve. However, the initial voltage $V_I$ is preferably a level that generates pseudospontaneous activity in the auditory nerve but does not generate a detectable auditory percept for the patient. Likely, the initial voltage $V_I$ will be below a prescribed or desired voltage level $V_D$ shown in FIG. 8. The desired voltage level $V_D$ of the PDS is one that reduces and preferably substantially suppresses tinnitus in the patient. Accordingly, the desired voltage level $V_D$ may vary by patient or may be within a tolerance range suitable for substantially all patients. In addition, the desired voltage level $V_D$ of the PDS could be one that suppresses a ratio or percentage of the detectable tinnitus, such as 50%.

As shown in FIG. 8, the initial voltage $V_I$ is applied to the patient at time t equal zero (0) and the desired voltage level $V_D$ is reached at a later exemplary time T1 using a PDS voltage application pattern 802. An envelope or boundary 804 passes through voltage level $V_N$ at time zero and represents a voltage level of the PDS that is insufficient to suppress tinnitus but sufficient to generate an audible percept to the patient. Accordingly, any point above the envelope 804 shown in FIG. 8 will generate an audible percept for the patient and any point below the envelope 804 will not generate an audible percept to the patient. As described above, the Applicants initially determined that an application of the PDS at the desired voltage level $V_D$ generated an uncomfortable audible noise relative to the first type of tinnitus patients for an approximate period of 60 seconds or more. At similar applied levels, Applicants determined for the second type of tinnitus patients that inaudible or slightly audible noise resulted. However, the audible noise is likely related to the desired voltage $V_D$ or current level. Thus, the PDS voltage application pattern 802 according to the first preferred embodiment of the controlled application step to suppress tinnitus can be any process that moves the patient from the initial voltage $V_I$ at time zero to the desired voltage $V_D$ at the later time T1 while remaining below the envelope 804. Accordingly, the time T1 preferably extends beyond an initial transient state an could equal, for example 90 seconds or more. The desired voltage level $V_D$ may change for the patient over time. However, an optimal or preferred $V_D$ (e.g., a lowest) may be selected from among voltages that effectively suppress tinnitus. Exemplary applications of the PDS voltage application pattern 802 can include a linear pattern, non-linear patterns including exponential patterns, continuous or intermittent positively sloped increments including discrete stepped voltage levels or the like. In addition, the PDS voltage application pattern 802 varies intensity of the voltage over time. However, the present invention is not intended to be so limited. For example, the PDS pattern could be a power variation over time or a current variation over time to transition the patient from an initial application level to a desired level sufficient to suppress tinnitus without generating additional sensations. From step S720, control continues to step S730.

In step S730, it is determined whether the applied PDS generates an audible percept. Preferably, in step S730 the patient is asked whether the audible percept can be heard. For example, the patient can be asked: a) can you hear any unusual sounds coming from the stimulation; and b) what is the quality and quantity of any sounds or tinnitus you hear during stimulation? If the determination in step S730 is negative, control continues to step S740. In step S740, it is determined whether the PDS is at the desired voltage level $V_D$. Alternatively, step S740 could be accomplished by asking the patient if the tinnitus is suppressed. For example, the patient can be asked: a) can you still hear your tinnitus? and b) what is the quality and quantity of any sounds or tinnitus you hear during stimulation? Such an alterative can be used even in cases where the desired voltage level $V_D$ is not known ahead of time. Further, the determination in step S740 could be whether the tinnitus is sufficiently suppressed to a prescribed level such as 50% or to a prescribed loudness magnitude.

During round window stimulation in step S740, loudness matching to a tone presented to the contralateral ear are preferably assessed for both tinnitus and any electrically-induced percepts at all stimulus levels to complement the scaling measures during the assessment period of step S710. In addition, sound-field pure-tone thresholds measured with contralateral masking can assess any possible threshold shift induced by the stimulus. Threshold measures will be repeated with and without electrical stimulation to control for the small conductive hearing loss produced by the myringotomy and electrode placement. Post-stimulus suppression and recovery effects are also preferably measured and classified in a manner similar to post-acoustic masking recovery.

In step S740, additional measurements of the PDS can preferably include current monitoring at the electrode. For subjects undergoing round window stimulation, a current generated by the applied voltage level of the PDS can be monitored, for example, in two ways. First, a battery-powered oscilloscope could constantly monitor the current flowing through the transtympanic electrode. In the first type tinnitus suppression using an inner ear implant, the processor of a cochlear implant for example can be calibrated with both in vitro resistive and realistic in vivo loads so that an approximate mapping from the clinical units used by the programming software to the current applied is generated. Such a mapping for the cochlear implant is obtained under the same PDS conditions that are used with promontory stimulation. Thus, prior to applying the PDS voltage level, an approximate current can be applied in the initial low setting is 50–75 microamperes. If the determination in step S740 is negative, the process continues to step S750.

In step S750, the voltage level of the PDS is increased and the current delivered during the stimulation is preferably constantly monitored and measured. Preferably, the voltage level of the PDS is increased according to a prescribed pattern. The same preset stimulus can be used across subjects along with monitoring a degree of tinnitus suppression and duration of any recovery effect. Accordingly, alternative patterns can be determined, evaluated and compared. From step S750, control returns to step S730.

If the determination in step S730 is affirmative, control continues to step S760. In step S760, another pattern for applying the PDS is selected and control returns to step S720. Alternatively, in step S760 a user defined stimulus with or without monitoring could be selected and used. If the determination in step S740 is affirmative, the process continues to step S770. Then, in step S770 control returns to step S640. The first preferred embodiment of the controlled application step S630 shown in FIG. 7 could further include a feed back loop such that a plurality of successful patterns are evaluated and quantitatively and qualitatively compared.

Figure 9:
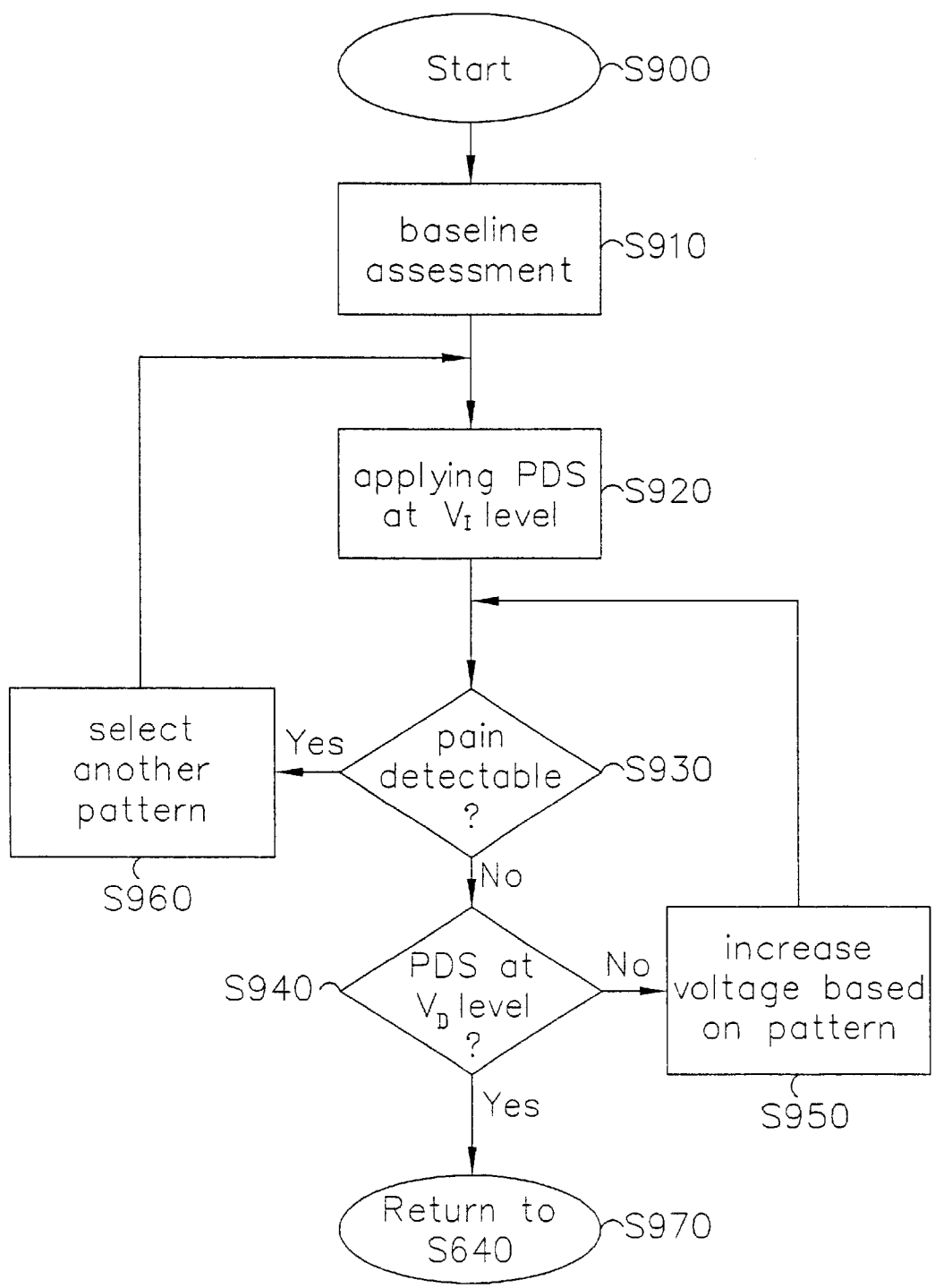
FIG. 9 is a diagram of a flowchart showing another preferred embodiment of a controlled application process to suppress tinnitus in an auditory nerve.

FIG. 9 shows a second preferred embodiment of the controlled application process of step S630 to suppress tinnitus in an auditory nerve. In step S900, the process begins. From step S900, control continues to step S910 where an appropriate baseline measurement of the hearing and tinnitus levels of the auditory nerve of the patient is performed. The process in step S910 can be similar to the process in step S710. From step S910, control continues to step S920.

Figure 10:
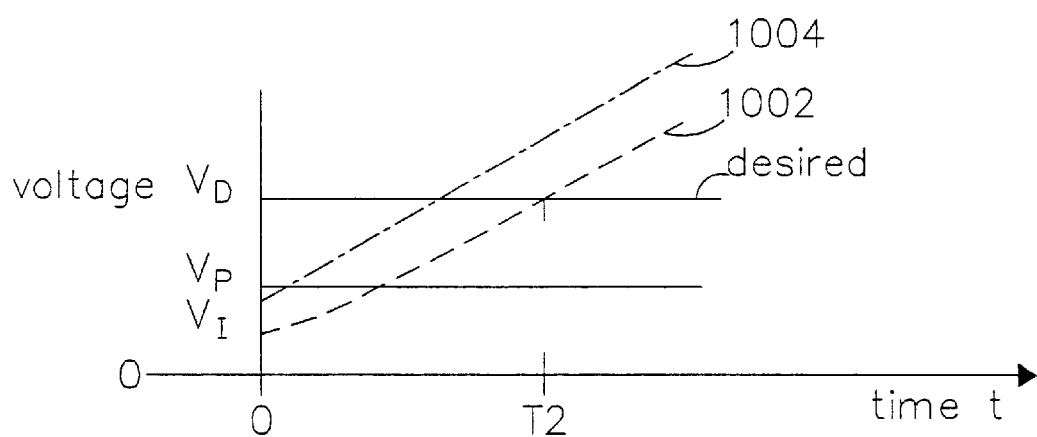
FIG. 10 is a diagram showing another exemplary driving signal voltage application pattern.

In step S920, application of the PDS signal at an initial voltage $V_I$ is provided to the auditory nerve of the patient. For example, as shown in FIG. 10, the initial voltage $V_I$ can be any level that preferably does not generate a detectable level of pain for the patient. Likely, the initial voltage $V_I$ will be below a prescribed or desired voltage level $V_D$ shown in FIG. 10. The desired voltage level $V_D$ of the PDS is preferably a lowest level voltage that reduces or substantially suppresses tinnitus in the patient.

As shown in FIG. 10, the initial voltage $V_I$ is applied to the patient at time t equal zero (0) and the desired voltage level $V_D$ is reached at a later exemplary time T2 using a PDS voltage application pattern 1002. An envelope or boundary 1004 passes through voltage level $V_P$ at time zero and represents a voltage level of the PDS that is insufficient to suppress tinnitus but sufficient to generate pain detected by the patient. Accordingly, any point above the envelope 1004 shown in FIG. 10 will generate detectable or perceptible pain for the patient and any point below the envelope 1004 will not generate pain. As described above, the Applicants determined that an initial application of the PDS at the voltage level $V_D$ generated an uncomfortable to severe level of pain for an approximate period of seconds for the second type of tinnitus patients. However, the pain is likely related to the desired voltage level $V_D$ or a desired current level. Thus, the PDS voltage application pattern 1002 according to the second preferred embodiment of the controlled application step to suppress tinnitus can be any process that moves the patient from the initial voltage $V_I$ at time zero to the desired voltage $V_D$ at the later time T2 while remaining below the envelope 1004. Accordingly, the time T2 preferably to extends beyond an initial transient state and could equal, for example 2 seconds or more. Exemplary applications of the PDS voltage application pattern 1002 can include a linear pattern, non-linear patterns including exponential patterns, continuous or intermittent positively sloped increments including discrete stepped voltage levels or the like. From step S920, control continues to step S930.

In step S930, it is determined whether the applied PDS generates detectable pain. Preferably, in step S930 the patient is asked whether the pain is present and to describe the pain. For example, the patient can be asked: a) can you describe the pain level resulting from the stimulation; and b) what is the quality and quantity of any pain felt or tinnitus heard during stimulation? If the determination in step S930 is negative, control continues to step S940. Steps S940 through step S970 are similar to steps S740 through step S770 of the first preferred embodiment of the controlled application to suppress tinnitus in an auditory nerve. Accordingly, a detailed description is omitted. It should be noted that the tinnitus suppression of step S940 likely happens after a delay of 60 to 90 seconds or more after reaching the desired voltage $V_D$.

Figure 11:
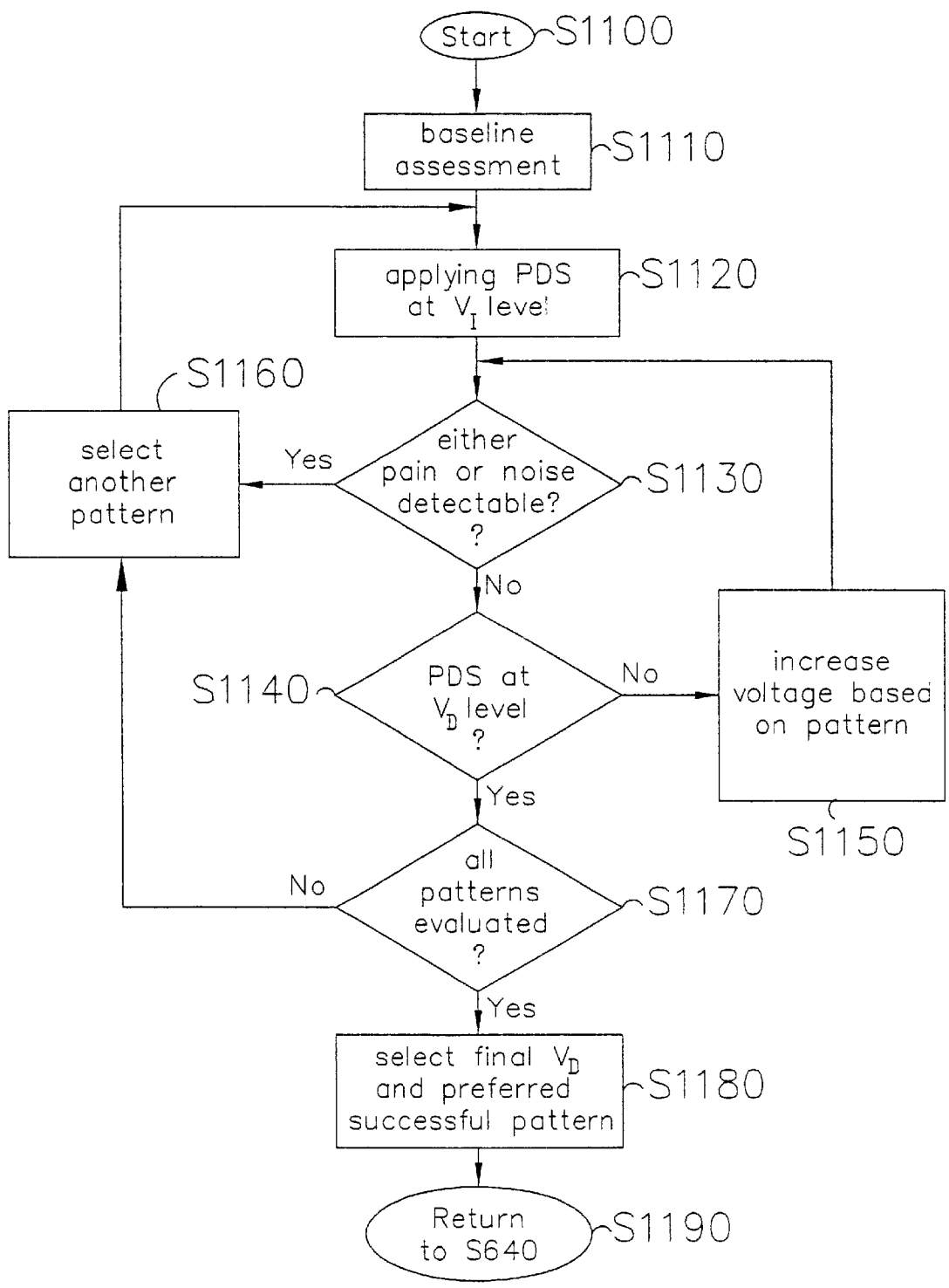
FIG. 11 is a diagram of a flowchart showing another preferred embodiment of a controlled application process to suppress tinnitus in an auditory nerve.

FIG. 11 shows a third preferred embodiment of the controlled application process of step S630 to suppress tinnitus in an auditory nerve. As shown in FIG. 11, step S1100 through step S1160 are similar to step S700 through step S760, and step S900 through step S960 of the first and second preferred embodiments of the controlled application to suppress tinnitus in an auditory nerve, respectively. Accordingly, a detailed description is omitted. However, in step S1130, detectable noise and/or pain can be concurrently or sequentially evaluated for all tinnitus patients. If the determination in step S1140 is affirmative, control continues to step S1170.

In step S1170, it is determined whether all possible patterns of a plurality of pattern such as a PDS voltage application or power application pattern have been evaluated. If the determination in step S1170 is negative, control returns back to step S1160 where another pattern is selected. If the determination in step S1170 is affirmative, control continues to step S1180. In step S1180, the successful patterns as described above are compared and a preferred pattern is quantitatively or qualitatively determined and then selected. Further, a final desired voltage $V_D$ can be determined. In other words, the desired voltage $V_D$ may vary by patient and accordingly a preferred final desired voltage $V_D$ can be quantitatively or qualitatively selected. From step S1180, control continues to to step S1190. Then, in step S1190 control returns to step S640.

Figure 12:
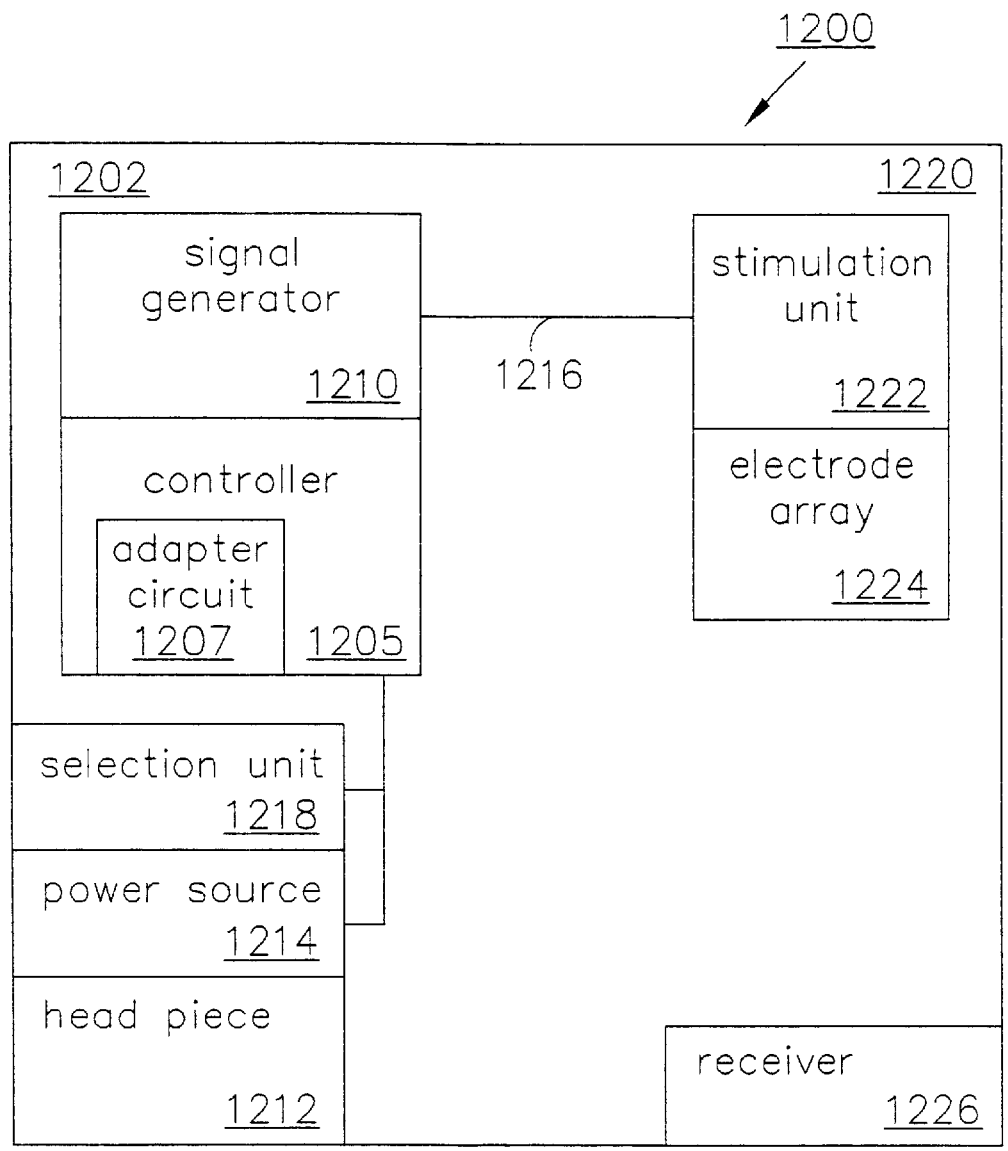
FIG. 12 is a diagram showing a preferred embodiment of an apparatus that provides a substantially imperceptible driving signal to the auditory nerve according to the present invention.

A second preferred embodiment of an apparatus to generate and substantially imperceptibly apply a pseudospontaneous driving signal to an auditory nerve according to the present invention will now be described. As shown in FIG. 12, the second preferred embodiment includes an inner ear stimulation system 1200 that directly electrically stimulates the auditory nerve (not shown). The inner ear stimulation system 1200 can include two components: (1) a wearable or external system, and (2) an implantable system. An external system 1202 includes a signal generator 1210. The signal generator 1210 can include a battery, or an additional equivalent power source 1214, and further includes electronic circuitry, typically including a controller 1205 that controls the signal generator 1210 to produce prescribed electrical signals.

The signal generator 1210 produces a driving signal or conditioner 1216 to generate pseudospontaneous activity in the auditory nerve. For example, the signal generator can produce a pseudospontaneous driving signal (PDS) in accordance with the first preferred embodiment. The signal generator 1210 can be any device or circuit that produces a waveform that generates pseudospontaneous activity. That is the signal generator 1210 can be any device that selects the PDS. For example, an application program operating on a special purpose computer or microcomputer combined with an A/D converter, and LC resinating circuit, firmware or the like can be used, depending on the exact form of the pseudospontaneous driving signal. Further, the inner ear stimulation system 1200 can preferably suppress, effectively alleviate or eliminate tinnitus in a patient without generating additional sensory percepts. The signal generator 1210 can vary parameters such as the frequency, amplitude, pulse width of the driving signal 1216. The external system 1202 can be coupled to a head piece 1212. For example, the head piece can be an ear piece worn like a hearing aid or surgically implanted under the skin behind the ear. Alternatively, the external system 1202 can be a separate unit.

As shown in FIG. 12, the controller 1205 is preferably implemented on a microprocessor. However, the controller 1205 can also be implemented on a special purpose computer, microcontroller and peripheral integrated circuit elements, an ASIC or other integrated circuit, a hardwired electronic or logic circuit such as a discrete element circuit, a programmable logic device such as a PLD, PLA, FGPA or PAL, or the like. The controller 1205 includes an adaptor circuit 1207. However, the adaptor circuit 1207 can be a separate unit from the controller 1205 in the external system 1202, outside the external system 1202 or as part of the implantable system 1220. In general, any device on which a finite state machine capable of controlling a signal generator and implementing the flowchart shown in FIGS. 6–7, 9 and 11 can be used to implement the controller 1205.

As shown in FIG. 12, the implantable system 1220 of the inner ear stimulation system 1200 can include a stimulator unit 1222 directly coupled to the auditory nerve. For example, the stimulator unit 1222 can include an electrode array 1224 or the like for implantation into the cochlea of a patient. The electrode array 1224 can be a single electrode or multiple electrodes that stimulate several different sites at arranged sites along the cochlea to evoke nerve activity normally originating from the respective sites. Preferably, the single electrode is adapted to be affixed as close to the round window to allow stimulation of the auditory nerve and cochlea according to the PDS voltage application pattern The stimulation unit 1222 is preferably electrically coupled to the auditory nerve. The stimulation unit 1222 can be located in the inner ear, middle ear, ear drum or any location that effectively couples the stimulation unit 1222 to the auditory nerve directly or indirectly, and produces pseudospontaneous activity in the auditory nerve caused by the stimulation unit 1222. In addition, the implantable system 1220 can be directly or indirectly coupled to the external system 1202.

If indirectly coupled to the external system 1202, the stimulator 1222 can include a receiver 1226. The receiver 1226 can receive information and power from corresponding elements in the external system 1202 through a tuned receiving coil (not shown) attached to the receiver 1226. The power, and data as to which electrode to stimulate, and with what intensity, can be transmitted across the skin using an inductive link from the external signal generator 1210. For example, the receiver 1226 can then provide electrical stimulating pulses to the electrode array 1224. Alternatively, the stimulation unit 1222 can be directly coupled to the external system 1202 via a conductive medium or the like.

The patient's response to electrical stimulation by the driving signal 1216 can be subsequently monitored or tested. The results of these tests could be used to modify the driving signal 1216 or to select from a plurality of driving signals using a selection unit 1218.

Figure 13:
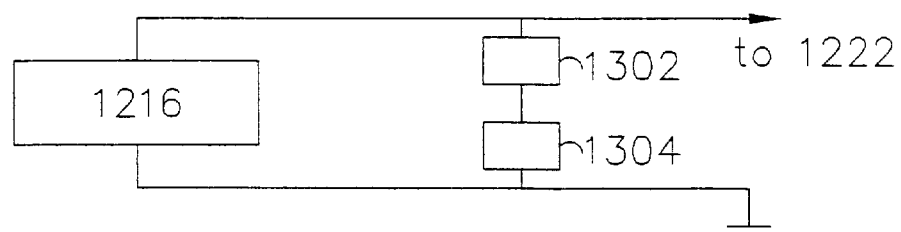
FIG. 13 is a diagram showing an exemplary adaptor circuit of the apparatus of FIG. 12.

In particular, according to the second preferred embodiment of an apparatus to generate and substantially imperceptibly apply a pseudospontaneous driving signal to an auditory nerve, the adaptor circuit 1207 is provided to transition through an initial transient state upon application of the PDS. The adaptor circuit 1207 can control, for example, according to the PDS voltage application pattern 1002 shown in FIG. 10, application of the desired voltage level $V_D$ to suppress tinnitus. An exemplary circuit for the adaptor circuit 1207 is shown in FIG. 13. As shown, the adaptor circuit 1207 is coupled to the driving signal 1216 used for the electrical stimulation. As shown in FIG. 13, the adaptor circuit 1207 includes series coupled switch 1302 and resistance unit 1304. The resistance unit 1304 is preferably a variable resistance unit that is selectively coupled to the driving signal 1216. As the resistance of the variable resistance unit 1304 is varied while coupled to the driving signal 1216, a controlled increased current will be diverted from the stimulation unit 1222. The adapter circuit 1207 may also include a user controllable adjuster unit or mechanism (not shown) to enable the user to control the adjustment or select a pattern. A built-in safety mechanism would be included in the adapter circuit 1207 to ensure the patient cannot cause injury. Thus, any one of a plurality of driving signals 1216 including a linear pattern, non-linear patterns like exponential patterns, continuous or intermittent positively sloped increments including discrete stepped voltage levels or the like can be provided using the adaptor circuit to the stimulation unit 1222.

When the stimulation unit 1222 includes the electrode array 1224, the stimulator unit 1222 can operate in multiple modes such as, the "multipolar" or "common ground" stimulation, and "bipolar" stimulation modes. However, the present invention is not intended to be limited to this. For example, a multipolar or distributed ground system could be used where not all other electrodes act as a distributed ground, and any electrode could be selected at any time to be a current source, current sink, or to be inactive during either stimulation phase with suitable modification of the receiver-stimulator. Thus, there is great flexibility in choice of stimulation strategy to provide the driving signal 1216 to the auditory nerve. However, the specific method used to apply the driving signal must result in the pseudospontaneous activity being generated. In addition, the present invention is not intended to be limited to a specific design of the electrode array 1224, and a number of alternative electrode designs as have been described in the prior art could be used.

The preferred embodiments according to the present invention are described above primarily with respect to a controlled voltage. However, a current source or current controlled stimulation is preferable for generating nerve responses. Movement of the electrode or the type of surrounding tissue can effect impedance and accordingly effect an applied voltage and for example, reproducible results.

Figure 14:
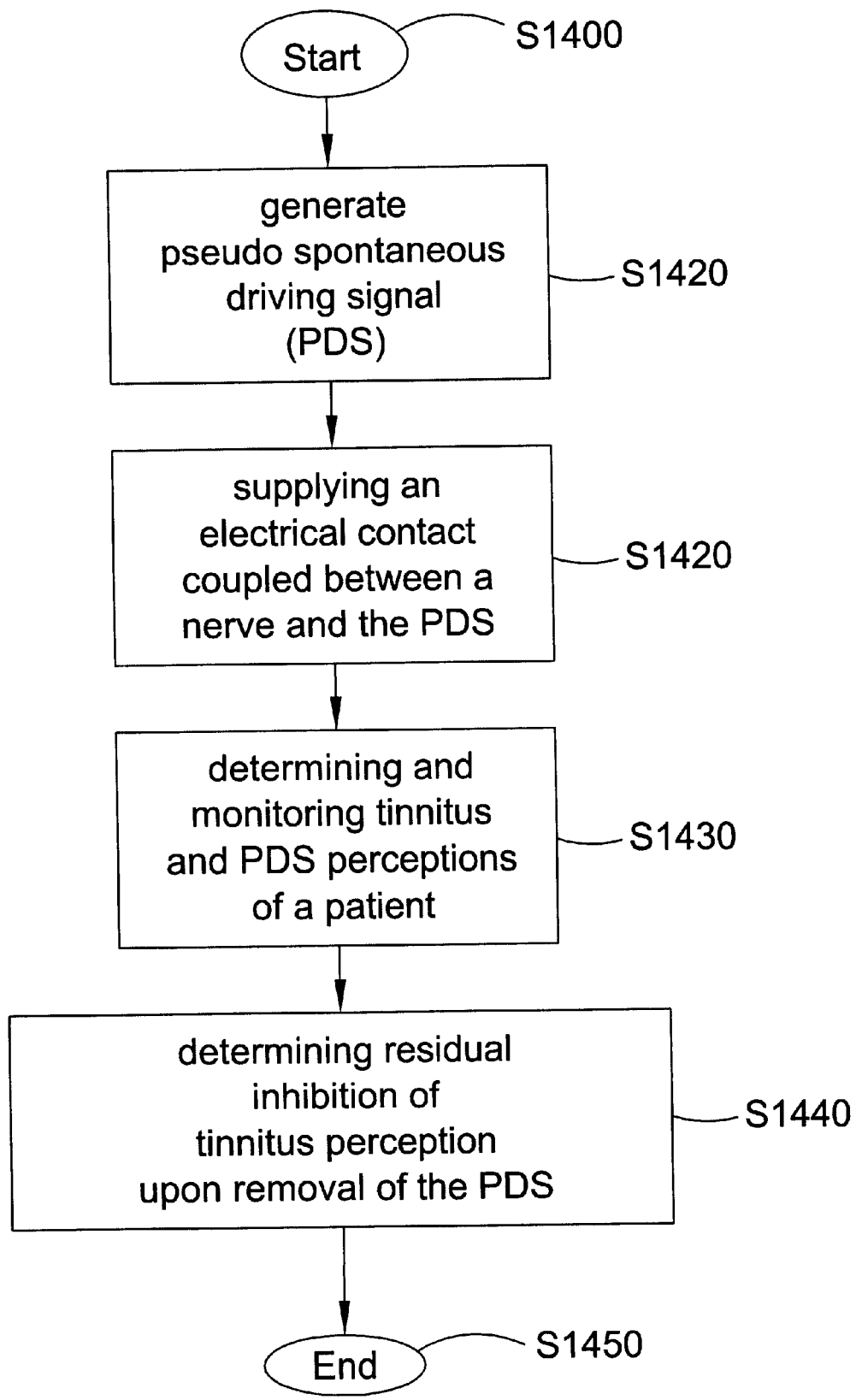
FIG. 14 is a diagram of a flowchart showing a preferred embodiment of a method of selecting human candidates for tinnitus reduction using a neural prosthetic.

A first preferred method for diagnosing candidates for neural prosthetics in treatment of tinnitus according to the present invention will now be described. As shown in FIG. 14, the process starts in step S1400. From step S1400, control continues to step S1410. In step S1410, a pseudo-spontaneous driving signal (PDS) is generated. For example, a driving signal according to the first preferred embodiment for diagnosing candidates can be generated or selected via a selection unit. An exemplary stimulus paradigm for a high-rate pulse train stimulation excepting the amplitude, frequency or interpulse period, which can be adjusted, is shown in FIG. 3. The high rate pulses 302 have a constant amplitude, pulse width and frequency of approximately 5 kHz as shown in FIG. 3. From step S1410, control continues to step S1420.

In step S1420, an electrical contact is preferably coupled between a nerve such as the auditory nerve in the ear of a patient and the PDS. The electrical contact can be, for example, a temporary single electrode provided to the middle ear region and preferably at or near the round window as well as the cochlea. Further, a middle ear implant or inner ear implant electrically coupled to the auditory nerve and cochlea or the like can be used. From step S1420, control continues to step S1430.

In step S1430, the application of the PDS is controlled or tuned to generate a desired activity in the nerve of a patient, for example, generating pseudospontaneous stimulation of the auditory nerve for suppressing tinnitus in the auditory nerve.

Figure 15:
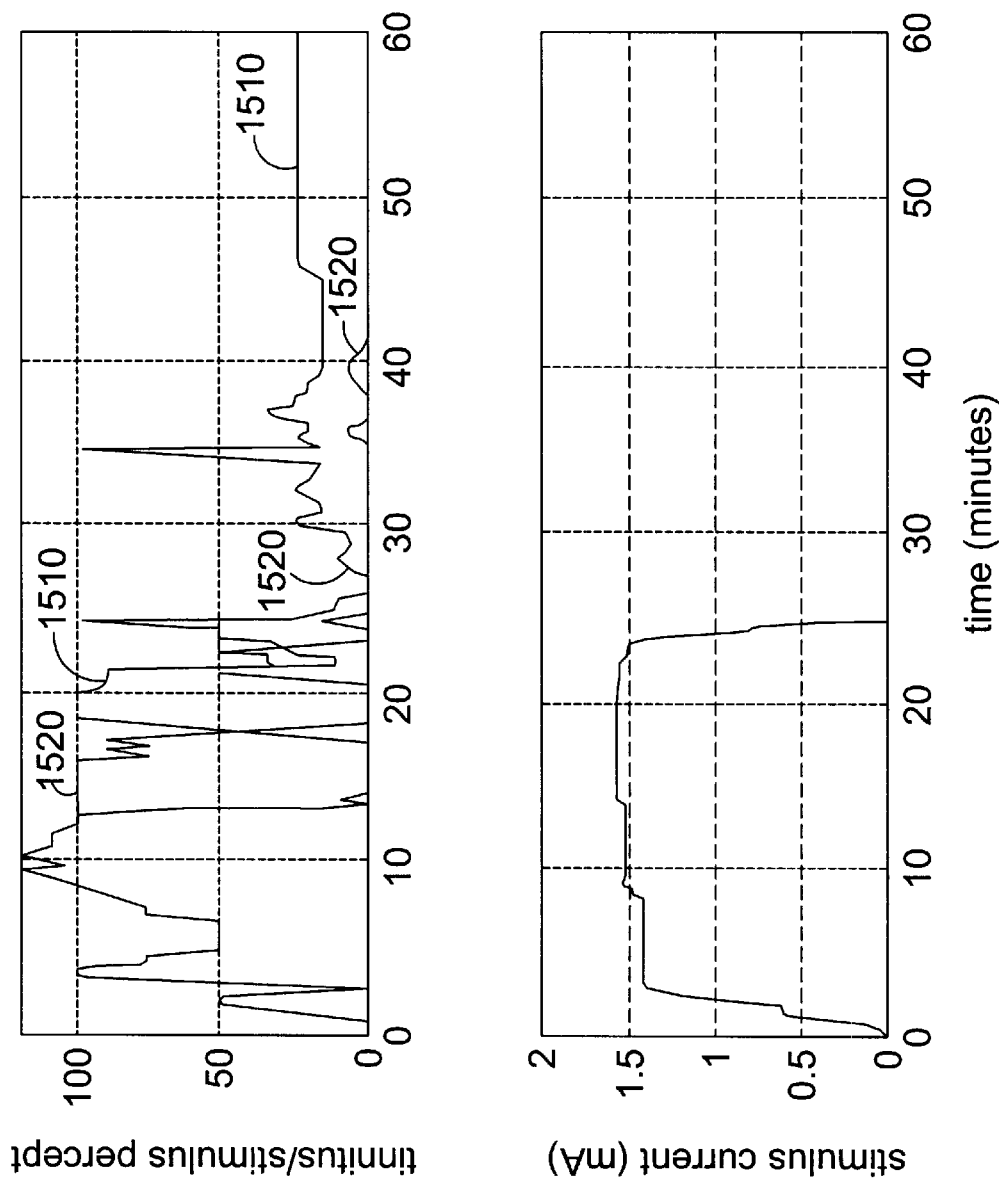
FIG. 15 is a diagram showing an exemplary relationship between tinnitus and stimulus perceptions upon application of an electrical signal capable of generating PSA in an auditory nerve.

In step 1430, during the controlled application of the PDS, tinnitus and the PDS (stimulus) perception of a patient are determined and monitored. Preferably, a time-course of tinnitus suppression and recovery is continuously or periodically (e.g., every 30 second interval) monitored during application of the PDS. The PDS can be varied, for example, using similar modalities or variations described above with respect to the preferred embodiments of FIGS. 6–11 and using devices, for example, similar to the preferred embodiments of FIGS. 12–13. An exemplary relationship between tinnitus and stimulus perceptions of a patient are shown in FIG. 15. As shown in FIG. 15, a stimulus percept 1510 and a tinnitus percept 1520 are shown. Transtympanic electrical stimulation of the round window using a stimulus frequency of 4800 Hz. 80 μs/phase is shown. The perception of the stimulus 1510 is followed by rapid adaptation and subsequent suppression of tinnitus percept 1520. The relationship between stimulus intensity and tinnitus loudness can be determined and evaluated. For example, a "best intensity" can be identified. Further, multiple stimulus frequencies and intensities can be used prior to the PDS and single-blind false trials can be used to perform placebo control. From step S1440, control continues to step S1450 where the PDS signal is terminated and substantial and/or residual inhibition of tinnitus perceived by a patient, if any, is determined. From step S1450, control continues to step S1460 where the process ends. However, the present invention is not intended to be so limited. For example, the process of steps S1410–S1450 can be repeated in part or in total, preferably after residual inhibition of tinnitus has passed for a patient. In addition, step S1430 could be repeated for evaluation before continuing to step S1440.

Currently, there is no predictive indicator for the successful masking of tinnitus. Suppression of tinnitus in the substantial or complete absence of a stimulus percept and/or residual inhibition after the stimulus percept can be diagnostic indications for selection of permanent neural prosthetics in treatment of tinnitus according to the preferred embodiments of the present invention. Thus, complete suppression, suppression below a threshold, or a significant reduction in tinnitus and/or PDS percept according to the preferred embodiment of FIG. 14 can diagnose subsequent treatment, for example, by neural prosthetics.

Preliminary studies by the Applicants showed remarkable but temporary auditory and sensory perceptual effects of a high frequency neural stimulation in human subjects. In one study by Applicants, ten volunteer human subjects with bothersome tinnitus and high-frequency sensorineural hearing loss underwent myringotomy and temporary placement of a round window electrode. Myringotomy was performed under topical phenol anesthesia and a custom-built platinum ball electrode was placed in the round window niche. Testing sessions typically lasted two to three hours. High-rate pulse train stimuli were presented at various stimulus intensities and tinnitus and stimulus perception were scaled by the subject (see step S1430). Five of ten subjects showed substantial or complete tinnitus suppression with either no perception or only a transient perception of the stimulus. Three showed tinnitus suppression only in association with the perception of the stimulus. Two showed no effects on tinnitus. Though lacking an ideal placebo-control, the results indicate a diagnostic for a clinically useful intervention of tinnitus.

The ten adults with high frequency sensorineural hearing loss and normal speech discrimination in an ear with disturbing tinnitus were chosen so that any deafferented auditory neurons are located in the basal cochlea, near the round window and presumably accessible to electrical stimulation from the middle ear. Common etiologies would include presbycusis, noise-induced hearing loss, and aminoglycoside ototoxicity. The possibility exists to correlate tinnitus suppression results with preoperative psychoacoustic measures; a process that could be critical to subsequent patient selection. Representative clinical details from the subjects are provided in Table 1.

TABLE 1

| subject | etiology | THQ | annoy-ance | loudness | pitch | response |
|---|---|---|---|---|---|---|
| NG | NIHL | 21 | 30–90 | 29 dB | 5 kHz | suppress |
| JH | NIHL | 13 | 20 | 6 dB | 5.3 kHz | mask |
| TK | NIHL | 33 | 35 | 4 dB | 11.5 kHz | mask |
| TS | presby-cusis | 19 | 80 | 4 dB | 7.3 kHz | suppress |
| RS | NIHL | 18 | 30–40 | 16 dB | 5.1 kHz | mask |
| JF | presby-cusis | 48 | 100 | 6 dB | 2.5 kHz | suppress |
| JG | NIHL | 28 | 60 | 2.5 dB | 10 kHz | suppress |
| PP | NIHL | 24 | 10–15 | 17 dB | 0.11 kHz | pain |
| RH | NIHL | 42 | 80 | 34 dB | 4.28 kHz | suppress |
| RB | NIHL | ?? | 40 | 4.5 dB | 7.2 kHz | none |

As shown in Table 1, THQ is score on tinnitus handicap questionnaire. Annoyance is subjective scaling. Loudness match is in dB SL (corrected for hearing threshold).

The controlled application in step 1430 of the preferred embodiment of FIG. 14 preferably includes a baseline assessment for example, as described with respect to preferred embodiments of FIG. 7 and in particularly in step S710. Further, preferred embodiments of FIG. 14 can include the tuning described in the preferred embodiment of FIG. 6 and in particular step S630 for example in order to preferably accomplish the application of the PDS to the nerve without generating additional sensations.

Results of testing by Applicants demonstrate test subjects fall into at least three categories of relationships between the PDS signal (e.g., stimulus or test signal) and effect on tinnitus, being (1) no response, (2) masking or (3) suppression. In the first case, in one subject of the ten subjects, no perception of the stimulus, pain or tinnitus effect could be elicited up to the maximal current output of the stimulator (i.e., >1.1 mA at 80 $\mu$s/phase). In another subject, stimulation above approximately 400 $\mu$A evoked pain, and no significant sound percept or tinnitus effect was noted below this pain threshold.

Figure 16:
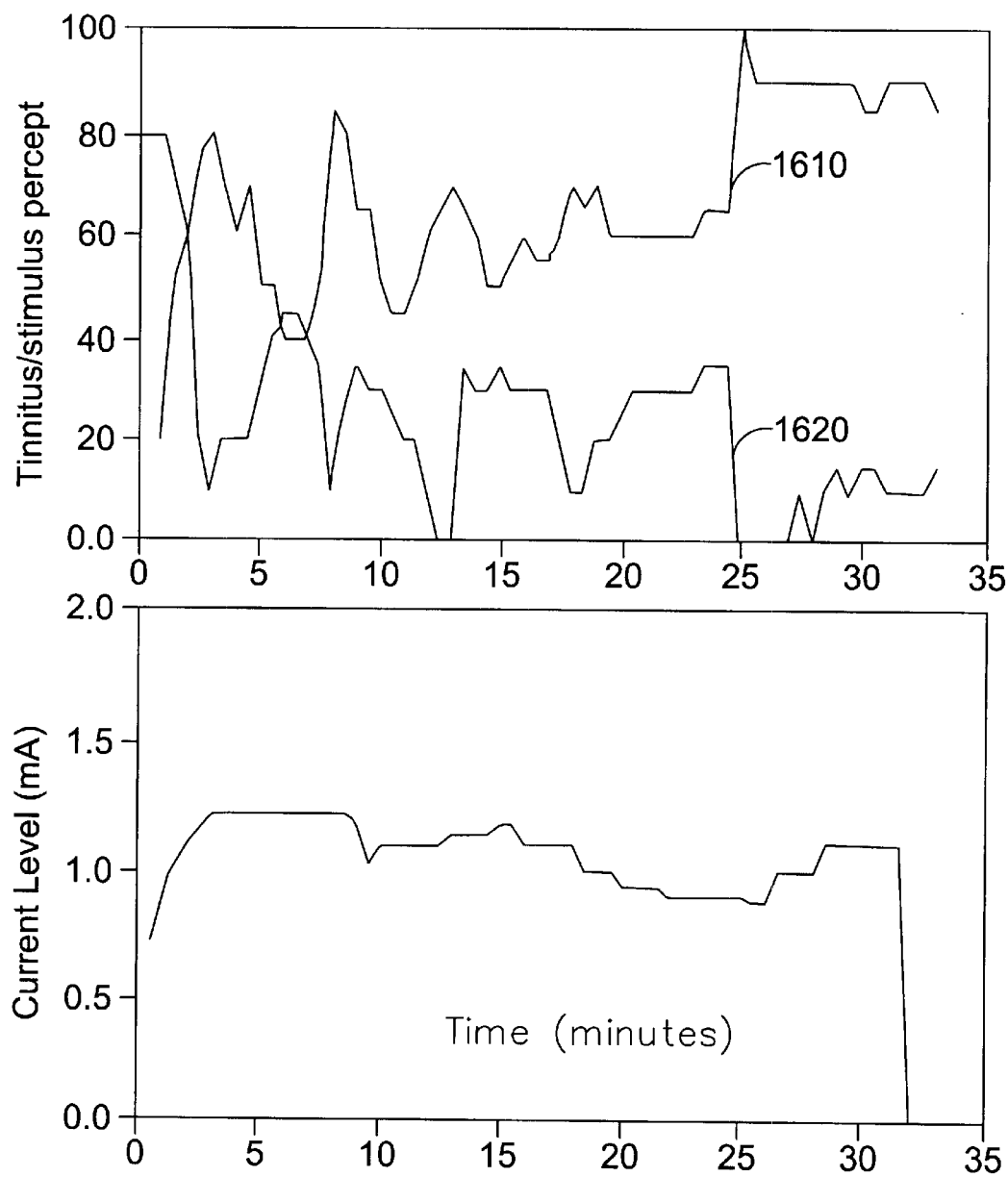
FIG. 16 is a diagram showing an exemplary relationship between tinnitus and stimulus perceptions upon application of an electrical signal capable of generating PSA in an auditory nerve.

Three test subjects showed electrical tinnitus masking by providing tinnitus suppression only in the presence of a stimulus percept. All noted the stimulus percept to sound similar to their underlying tinnitus. FIG. 16 illustrates an exemplary tinnitus percept 1620 and stimulus percept 1610 over time along with the stimulus current presented for one of the subjects. The masking relationship did not demonstrate any significant residual inhibition, and no particular subject preference for the stimulus percept over the underlying tinnitus was noted.

Figure 17:
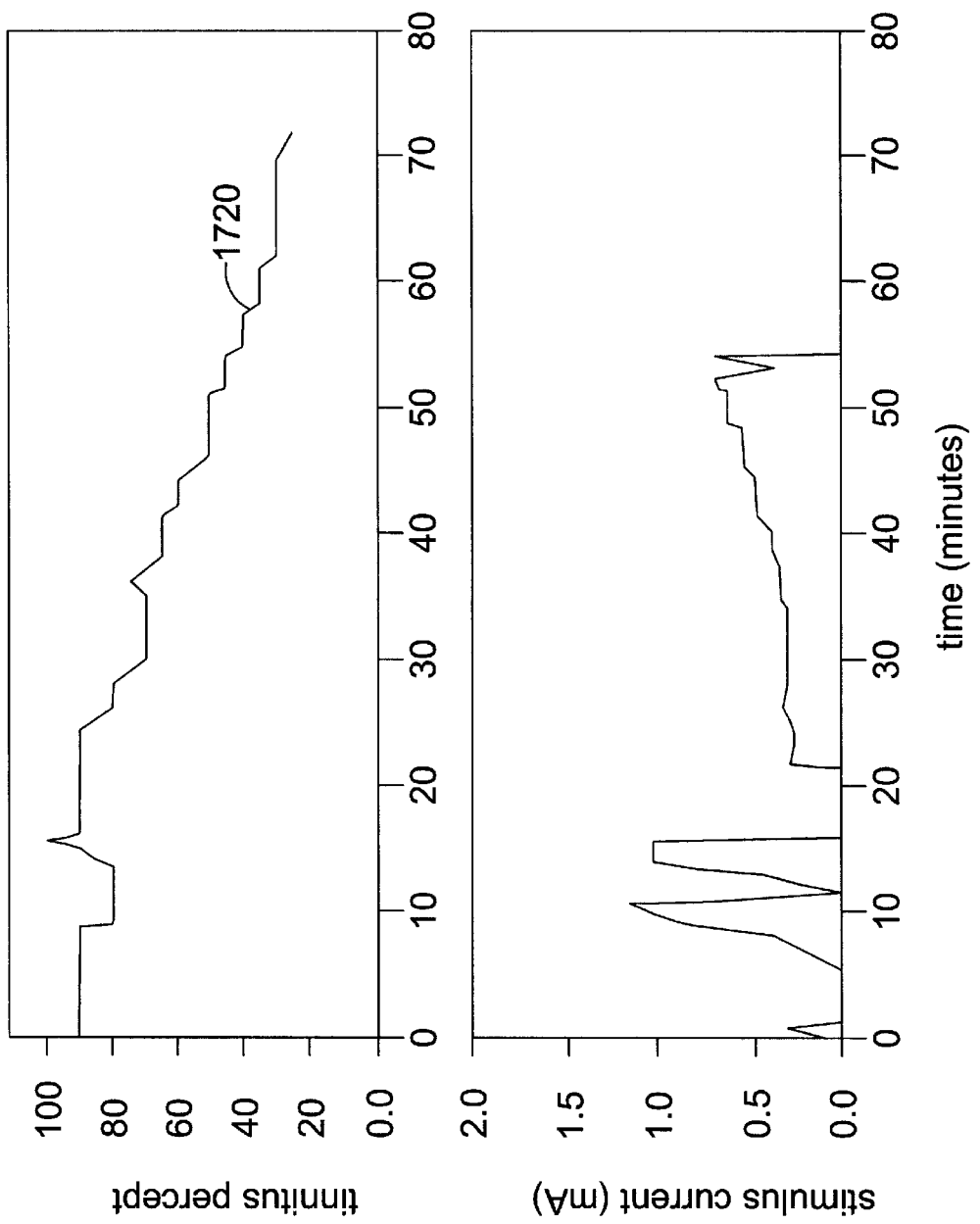
FIG. 17 is a diagram showing an exemplary tinnitus perceptions upon application of an electrical signal capable of generating PSA in an auditory nerve.

Five subjects in Applicants' study showed electrical suppression of tinnitus in the absence of a stimulus percept or after complete or nearly complete adaptation to the stimulus percept. Round window stimulation demonstrated a dramatic degree of adaptation to the unmodulated high-rate pulse trains in three of the subjects who initially perceived loud tinnitus-like sounds when the stimulus was ramped up. After several minutes, the stimulus perception adapted to zero or near zero followed shortly after by a decrement in the perceived tinnitus. There was a residual inhibition of lasting from two to seventy two hours in four of the subjects. FIGS. 14 and 17 demonstrate the tinnitus and stimulus percepts from two of these subjects. As shown in FIG. 17, transtympanic electrical stimulation of the round window used a stimulus frequency 4800 Hz, 40 $\mu$s/phase. No perception of the stimulus was apparent and 80% suppression of tinnitus 1720 was obtained. All five subjects who suppressed in this manner found clinically dramatic relief from the annoyance of their tinnitus and were subjectively pleased with the result.

Tinnitus suppression as induced in the five subjects appears to be a slow process and typically required between five and fifteen minutes of stimulation and residual inhibition lasted from hours to days. This is in contrast to the masking effects in the three subjects who masked, which were immediate. While unusually long, the residual inhibition reported here is not unreasonable and may in fact make clinical application of a tinnitus suppression device easier. Further, in one cochlear implant subject tested by Applicants tinnitus returns after more than twenty four hours.

The preferred embodiment of FIG. 14 provides an exemplary method of identifying candidates for treatment of tinnitus with permanent neural prosthetics as demonstrated in five of ten subjects, at least temporarily. While placebo-control in the current experimental paradigm is not ideal, it is not likely these five subjects are demonstrating significant placebo effects given the similarity of their responses to those of tinnitus subjects with cochlear implants for whom adequate placebo control has been possible and the placebo controls implemented. The placebo controls included multiple stimulus frequencies and intensities (not shown) that failed to suppress tinnitus prior to the acquisition of the data in FIGS. 15–17. The time-course of tinnitus suppression and recovery was closely monitored, and the pulse frequency was modified so as to eliminate desynchronized auditory neuron responses. Thus, high-rate electrical pulse trains applied to the round window can result in tinnitus suppression without an ongoing stimulus percept. Further, procedures are provided for determining or selecting candidates for tinnitus treatment through neural prosthetics, testing whether patient's tinnitus can be reduced and methods determining residual effects.

As described above, the preferred embodiments of a system and method for application of pseudospontaneous neural stimulation according to the present invention have various advantages. Heretofore, predictive treatment and/or reduction results for tinnitus were not possible. The preferred embodiments generate stochastically independent or pseudospontaneous neural activity, for example, in an auditory nerve to test or identify candidates for treatment of tinnitus. Further, such diagnosis according to the preferred embodiments of the present invention can monitor, use or select specific patterns of electrical to suppress tinnitus without producing an auditory percept and potential. Further, preferred embodiments according to the present invention can monitor residual suppression of tinnitus or stimulus percepts. Thus, an inner ear or middle ear auditory prosthesis can be provided that substantially imperceptibly suppresses tinnitus. In addition, the preferred embodiments provide an apparatus and method that delivers a prescribed signal such as a high rate pulse train to imperceptibly treats or generate neural pseudospontaneous activity and may be used in conjunction with a suitable auditory prosthesis to increase hearing capability by providing a prescribed signal to auditory neurons.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method of diagnosing whether a human is a candidate for tinnitus reduction using a neural prosthetic, comprising:
    applying a pseudospontaneous driving electrical signal capable of generating pseudospontaneous activity in an auditory nerve to an auditory nerve of a plurality of candidates;
    identifying a prescribed threshold; and
    selecting the candidate having an auditory response to said pseudospontaneous driving electrical signal and tinnitus perception below the prescribed threshold upon application of said pseudospontaneous driving electrical signal.

2. The method of claim 1, wherein the prescribed threshold is a percentage decrease of the tinnitus perception of the candidate.

3. The method of claim 1, wherein the prescribed threshold is substantially physiologically imperceptable to the candidate.

4. The method of claim 3, further comprising modifying the pseudospontaneous driving electrical signal to a sustained effective level while the pseudospontaneous driving electrical signal remains substantially physiologically imperceptible to the patient.

5. The method of claim 4, wherein the auditory response remains below the prescribed threshold for a prescribed time after removal of the pseudospontaneous driving electrical signal.

6. The method of claim 1, wherein the pseudospontaneous driving electrical signal includes one of (i) a pulse train generating substantially continuous activation, (ii) a broad band noise, or (iii) at least fluctuations in amplitude greater than prescribed amount at a frequency above approximately 2 k Hz.

7. The method of claim 1, wherein the applying step is performed by one of a middle ear implant and an inner ear implant, and comprises applying current to the auditory nerve, wherein the pseudospontaneous activity is demonstrated by statistically independent activity in a plurality of nerve fibers in the auditory nerve, and wherein the prescribed level is a 50% reduction of the tinnitus perception.

8. The method of claim 1, wherein the auditory nerve comprises a plurality of nerve fibers, and wherein the pseudospontaneous driving electrical signal comprises one or more signals that generate a substantially maximum firing rate of the plurality of nerve fibers.

9. A method of testing whether a patient's tinnitus can be at least partially reduced, comprising:
applying an electrical signal capable of generating pseudospontaneous activity in an auditory nerve of at least one human to the patient's auditory nerve;
determining the patient's response to said electrical signal; and
adjusting, if the patient's tinnitus is not at least partially reduced, a level of said electrical signal and repeating said determining step.

10. The method of claim 9, wherein the patient's tinnitus is below a prescribed threshold after said adjusting step.

11. The method of claim 9, wherein the electrical signal includes one of (i) a pulse train generating substantially continuous activation, (ii) a broad band noise, or (iii) at least fluctuations in amplitude greater than prescribed amount at a frequency above approximately 2k Hz.

12. An apparatus of diagnosing whether a human is a candidate for tinnitus reduction using a neural prosthetic, comprising:
applying means for applying an electrical signal capable of generating pseudospontaneous activity in an auditory nerve of at least one human to a plurality of candidates;
identifying means for identifying a prescribed threshold; and
selecting means for selecting the candidate having an auditory response to said electrical signal and tinnitus perception below the prescribed threshold upon application of said electrical signal.

13. A method of determining residual effects to a patient with tinnitus resulting from application of a signal capable of inducing pseudo-spontaneous activity, comprising:
applying an electrical signal capable of generating pseudo-spontaneous activity in an auditory nerve of at least one human to the patient's auditory nerve for a first time period; and
determining whether there remains a perceptible difference in the patient's tinnitus after said first time period.

14. The method of claim 13, wherein said determining comprises determining a second time period during which said perceptible difference remains.

15. The method of claim 13, wherein said determining comprises determining whether there remains a reduction in the patient's tinnitus.

16. The method of claim 13, wherein said determining comprises whether there remains a substantial elimination of the patient's tinnitus.

17. The method of claim 13, further comprising repeating said applying step and said determining step using a second time period.

18. The method of claims 13, wherein the electrical signal includes one of (i) a pulse train generating substantially continuous activation, (ii) a broad band noise, or (iii) at least fluctuations in amplitude greater than prescribed amount at a frequency above approximately 2 k Hz.

* * * * *